US010845366B2

(12) United States Patent
Gerner et al.

(10) Patent No.: US 10,845,366 B2
(45) Date of Patent: Nov. 24, 2020

(54) PREDICTIVE MARKERS FOR POLYAMINE INHIBITOR CANCER THERAPIES

(71) Applicant: ARIZONA BOARD OF REGENTS ON BEHALF OF THE UNIVERSITY OF ARIZONA, Tucson, AZ (US)

(72) Inventors: Eugene Gerner, Tucson, AZ (US); Edwin Paz, Durham, NC (US); Bonnie Lafleur, Tucson, AZ (US); Jenaro Garcia-Huidobro, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/172,252

(22) Filed: Oct. 26, 2018

(65) Prior Publication Data
US 2019/0113518 A1 Apr. 18, 2019

Related U.S. Application Data

(63) Continuation of application No. 14/438,999, filed as application No. PCT/US2013/067305 on Oct. 29, 2013, now Pat. No. 10,151,756.

(60) Provisional application No. 61/719,748, filed on Oct. 29, 2012.

(51) Int. Cl.
*G01N 33/574* (2006.01)
*A61K 45/06* (2006.01)
*A61K 31/192* (2006.01)
*A61K 31/196* (2006.01)
*A61K 31/198* (2006.01)
*A61K 31/616* (2006.01)
*A61K 31/635* (2006.01)
*C12Q 1/6886* (2018.01)
*C12Q 1/18* (2006.01)

(52) U.S. Cl.
CPC ..... *G01N 33/57496* (2013.01); *A61K 31/192* (2013.01); *A61K 31/196* (2013.01); *A61K 31/198* (2013.01); *A61K 31/616* (2013.01); *A61K 31/635* (2013.01); *A61K 45/06* (2013.01); *C12Q 1/18* (2013.01); *C12Q 1/6886* (2013.01); *G01N 33/57492* (2013.01); *C12Q 2600/106* (2013.01); *C12Q 2600/156* (2013.01); *C12Q 2600/158* (2013.01); *C12Q 2600/178* (2013.01); *G01N 2333/4703* (2013.01); *G01N 2800/52* (2013.01)

(58) Field of Classification Search
None
See application file for complete search history.

(56) References Cited

U.S. PATENT DOCUMENTS

| 4,309,442 A | 1/1982 | Bey et al. |
| 4,330,559 A | 5/1982 | Bey et al. |
| 4,413,141 A | 11/1983 | Bey et al. |
| 4,499,072 A | 2/1985 | Sunkara et al. |
| 4,859,452 A | 8/1989 | Ajani et al. |
| 4,925,835 A | 5/1990 | Heston |
| 5,002,879 A | 3/1991 | Bowlin et al. |
| 5,814,625 A | 9/1998 | Larson et al. |
| 5,843,929 A | 12/1998 | Larson et al. |
| 6,258,845 B1 | 7/2001 | Gerner et al. |
| 6,573,290 B1 | 6/2003 | Love |
| 6,602,910 B2 | 8/2003 | Levenson et al. |
| 6,753,422 B2 | 6/2004 | O'Brien et al. |
| 7,273,888 B2 | 9/2007 | Ramesh et al. |
| 7,592,319 B2 | 9/2009 | Li et al. |
| 8,329,636 B2 | 12/2012 | Gerner et al. |
| 9,072,778 B2 | 7/2015 | Bachmann |
| 9,121,852 B2 | 9/2015 | Gerner et al. |
| 9,937,141 B2 | 4/2018 | Gerner et al. |
| 2002/0081611 A1 | 6/2002 | O'Brien et al. |
| 2002/0110590 A1 | 8/2002 | Shaked et al. |
| 2005/0032726 A1 | 2/2005 | Li et al. |
| 2005/0059690 A1 | 3/2005 | Newman et al. |
| 2010/0197718 A1 | 8/2010 | Pisano et al. |
| 2010/0317708 A1 | 12/2010 | Gerner et al. |
| 2011/0256161 A1 | 10/2011 | Burns et al. |
| 2012/0259013 A1 | 10/2012 | Motwani et al. |
| 2013/0157972 A1 | 6/2013 | Cheng et al. |
| 2013/0164751 A1 | 6/2013 | Gerner et al. |

(Continued)

FOREIGN PATENT DOCUMENTS

| CA | 2 165 481 | 1/1995 |
| EP | 2 438 919 | 4/2012 |

(Continued)

OTHER PUBLICATIONS

Takamizawa et al. Cancer Research 64, 3753-3756, Jun. 2004 (Year: 2004).*
Viswanathan et al. Nature Genetics 41, 843-849, 2009 (Year: 2009).*
Meyskens et al. Cancer Prevention Research 1, 32-38 Jun. 2008 (Year: 2008).*
Zell et al. Clinical Cancer Research 15(19): 6208-6216, 2009 (Year: 2009).*
Piskounova et al. Cell 147, 1066-1079, Nov. 23, 2011 (Year: 2011).*
"VANIQA®" (eflornithine hydrochloride) Prescription Information, dated Jul. 2010.

(Continued)

*Primary Examiner* — Jeffrey S Lundgren
*Assistant Examiner* — Michael J Schmitt
(74) *Attorney, Agent, or Firm* — Parker Highlander PLLC

(57) ABSTRACT

The present invention relates to therapeutic methods and medical uses comprising the identification and use of cancer marker surrogates for increased polyamine expression. These markers may be used to identify patients who may be treated for diseases and disorders that are susceptible to polyamine synthesis inhibitors, and they can also be used to monitor therapeutic responses when such agents are used.

20 Claims, 11 Drawing Sheets

Specification includes a Sequence Listing.

(56) References Cited

U.S. PATENT DOCUMENTS

| | | |
|---|---|---|
| 2013/0216528 A1 | 8/2013 | Cheung et al. |
| 2013/0217743 A1 | 8/2013 | Raj et al. |
| 2015/0301060 A1 | 10/2015 | Gerner et al. |
| 2016/0213634 A1 | 7/2016 | Gerner et al. |
| 2017/0362658 A1 | 12/2017 | Gerner et al. |

FOREIGN PATENT DOCUMENTS

| | | |
|---|---|---|
| JP | 2002-509884 | 4/2002 |
| JP | 2012-511052 | 5/2012 |
| WO | WO 99/49859 | 10/1999 |
| WO | WO 01/68076 | 9/2001 |
| WO | WO 02/15895 | 2/2002 |
| WO | WO 2009/048932 | 4/2009 |
| WO | WO 2010/056919 | 5/2010 |
| WO | WO 2010/132817 | 11/2010 |
| WO | WO 2011/135459 | 11/2011 |
| WO | WO 2014/140072 | 9/2014 |
| WO | WO 2016/130918 | 8/2016 |
| WO | WO 2017/075576 | 5/2017 |

OTHER PUBLICATIONS

Alberts et al., "Do NSAIDs exert their colon cancer chemoprevention activities through the inhibition of mucosal prostaglandin synthetase?," J. Cell. Biochem. Supp., (22):18-23, 1995.
Arber et al., "A K-ras oncogene increases resistance to sulindac-induces apoptosis in rat enterocytes," Gastroenterology, 113: 1892-1990, 1997.
Babbar et al., "Induction of spermidine/spermine N1-acetyltransferase (SSAT) by aspirin in Caco-2 colon cancer cells," Biochem. J., 394:317-24, 2006.
Bachrach et al., "Polyamines: new cues in cellular signal transduction," News Physiol. Sci., 16:106-109, 2001.
Barry et al., "Ornithine decarboxylase polymorphism modification of response to aspirin treatment for colorectal adenoma prevention," J. Natl. Cancer Inst., 98(20):1494-500, 2006.
Basuroy and Gerner, "Emerging concepts in targeting the polyamine metabolic pathway in epithelial cancer chemoprevention and chemotherapy," J. Biochem., 139:27-33, 2006.
Bedi et al., "Inhibition of apoptosis during development of colorectal cancer," Cancer Res., 55(9):1811-1816, 1995.
Bello-Fernandez et al., "The ornithine decarboxylase gene is a transcriptional target of c-Myc," Proc. Natl. Acad. Sci. USA, 90:7804-8, 1993.
Boolbol et al., "Cyclooxygenase-2 overexpression and tumor formation are blocked by sulindac in a murine model of familial adenomatous polyposis," Cancer Research, 56:2556-2560, 1996.
Boone et al., "Biomarker end-points in cancer chemoprevention trails," IARC Scientific Publications, 142:273-280, 1997.
Boyle et al., "Polyamine contents in rectal and buccal mucosae in humans treated with oral difluoromethylornithine," Cancer Epidemiol. Biomarkers Prev., 1:131-135, 1992.
Brabender et al., "Upregulation of ornithine decarboxylase mRNA expression in Barrett's esophagus and Barrett's-associated adenocarcinoma," J. Gastroint. Surg., 5:174-181; discussion 182, 2001.
Braverman et al., "Ornithine decarboxylase: an unreliable marker for the identification of population groups at risk for colonic neoplasia," Am. J. Gastronenterology, 85:723-726, 1990.
Castel et al., "Treatment of high-risk neuroblastoma with anti-GD2 antibodies," Clinical and Translational Oncology, 12:788-793, 2010.
Childs et al., "Polyamine-dependent gene expression," Cell. Molec. Life Sci., 60:1394-1406, 2003.
Croghan et al., "Dose-related alpha-difluoromethylornithine ototoxicity," Am. J. Clin. Oncol., (14):331-5, 1991.
Derynck et al., "TGF-beta signaling in tumor suppression and cancer progression," Nature Genetics, 29:117-29, 2001.
DuBois et al., "G1 delay in cells overexpressing prostaglandin endoperoxide synthase-2," Cancer Res., 56:733-737, 1996.
Erdman et al., "Assessment of Mutations in Ki-ras and P53 in colon cancers from azoxymethane-and dimethylhydrazine-treated rats," Mol. Carcin., (19):137-144, 1997.
Erdman et al., "APC-dependent changes in expression of genes influencing polyamine metabolism, and consequences for gastrointestinal carcinogenesis, in the Min mouse," Carcinogenesis, 20(9):1709-13, 1999.
Fearon et al., "A genetic model for colorectal tumorigenesis," Cell, 61:759-767, 1990.
Fultz and Gerner, "APC-dependent regulation of ornithine decarboxylase in human colon tumor cells," Mol. Carcinog., 34:10-8, 2002.
Gamble et al., "Polyamine pathway inhibition as a novel therapeutic approach to treating neuroblastoma," Frontier in Oncology, 2(162):1-10, 2012.
Gann et al., "Low-dose aspirin and incidence of colorectal tumors in a randomized trial," J. Natl. Cancer Inst., 85:1220-1224, 1993.
Gerner and Meyskens, "Polyamines and cancer: old molecules, new understanding," Nature Rev. Cancer, 4:781-92, 2004.
Gerner et al., "Combination chemoprevention for colon cancer targeting polyamine synthesis and inflammation," Clinical Cancer Research, 15(3):758-761, 2009.
Gerner et al., "Gastrointestinal tissue polyamine contents of patients with Barrett's esophagus treated with alpha-difluoromethylornithine," Cancer Epidemiol. Biomarkers Prev., 3:325-330, 1994.
Gerner, "Impact of dietary amino acids and polyamines on intestinal carcinogenesis and chemoprevention in mouse models", Biochemical Society Transactions, 35(2):322-325, 2007.
Gerner et al. "Rationale for, and design of, a clinical trial targeting polyamine metabolism for colon cancer chemoprevention." Amino acids 33.2 (2007): 189-195.
Giardiello et al., "Ornithine decarboxylase and polyamines in familial adenomatous polyposis," Cancer Res., (57):199-201, 1997.
Greenberg et al., "Reduced risk of large bowel adenomas among aspirin users," J. Natl. Cancer Inst., 85:912-916, 1993.
Guo et al., "Functional analysis of human ornithine decarboxylase alleles," Cancer Res., 60(22):6314-6317, 2000.
Hanif et al., "Effects of nonsteroidal anti-inflammatory drugs on proliferation and on induction of apoptosis in colon cancer cells by a prostaglandin-independent pathway," Biochemical Pharmacology, (52):237-245, 1996.
Hessels et al., "Microbial flora in the gastrointestinal tract abolishes cytostatic effects of α-difluoromethylornithine in vivo," Int. J. Cancer, 43: 1155-1164, 1989.
Hixson et al., "Ornithine decarboxylase and polyamines in colorectal neoplasia and mucosa," Cancer Epidemiology Biomarkers Prev., 2:369-374, 1993.
Hixson et al., "Sources of variability in measurements of ornithine decarboxylase activity and polyamine contents in colorectal mucosa," Cancer Epidemoil. Biomarkers Prev., 3:317-323, 1994.
Hogarty et al., "ODC1 is a critical determinant of MYCN oncogenesis and a therapeutic target in neuroblastoma," Cancer Res., 68:9735-9745, 2008.
Hubner et al., "Ornithine decarboxylase G316A genotype is prognostic for colorectal adenoma recurrence and predicts efficacy of aspirin chemoprevention," Clin. Cancer Res., 14(8):2303-9, 2008.
Hughes et al., "Polyamines reverse non-steroidal anti-inflammatory drug-induced toxicity in human colorectal cancer cells", Biochem J, 374:481-8, 2003.
Ignatenko et al., "Dietary putrescine reduces the intestinal anticarcinogenic activity of sulindac in a murine model of familial adenomatous polyposis," Nutrition and Cancer, 56(2): 172-181, 2006.
Ignatenko et al., "Role of c-Myc in intestinal tumorigenesis of the ApcMin/+ mouse," Cancer Biol. Ther., 5(12):1658-64, 2006.
Iwamoto et al., "Expression of beta-catenin and full-length APC protein in normal and neoplastic colonic tissues," Carcinogenesis, 21:1935-40, 2000.
Jass et al., "Emerging concepts in colorectal neoplasia," Gastroenterology, 123:862-876, 2002.

(56) References Cited

OTHER PUBLICATIONS

Johnson et al. "Relationships between drug activity in NCI preclinical in vitro and in vivo models and early clinical trials." British Journal of Cancer 84.10 (2001): 1424.
Kawamori et al., "Chemopreventive activity of celecoxib, a specific cyclooxygenase-2 inhibitor, against colon carcinogenesis," Cancer Research, 58:409-412, 1998.
Kelloff et al., "Chemopreventive drug development: perspectives and progress," Cancer Epidemiology Biomarks and Prevention, 3:85-98, 1994.
Kelloff et al., "New agents for cancer chemoprevention," J. Cell. Biochem., 265:1-28, 1996.
Kelloff et al., "Perspectives on chemoprevention agent selection and short term clinical prevention trials," European J. Cancer Prevention, 5(Supp. 2):79-85, 1996.
Kingsnorth et al., "Effects of alpha-difluoromethylornithine and 5-fluorouracil on the proliferation of a human colon adenocarcinoma cell line," Cancer Res., 43(9):4035-8, 1983.
Kruh et al., "Expression Pattern of MRP in Human Tissues and Adult Solid Tumor Cell Lines," J. Natl. Cancer Inst., 87(16):1256-1258, 1995.
Ladenheim et al., "Effect of sulindac on sporadic colonic polyps," Gastroenterology, 108:1083-1087, 1995.
Lanza et al., "Peptic ulcer and gastrointestinal hemorrhage associated with nonsteroidal anti-inflammatory drug use in patients younger than 65 years. A large health maintenance organization cohort study," Arch. Intern. Med., 155:1371-1377, 1995.
Le et al., "Effects of socioeconomic status and treatment disparities in colorectal cancer survival," Cancer Epidemiol. Biomarkers Prev., 17:1950-62, 2008.
Levin et al., "Relationship between ornithine decarboxylase levels in anaplastic gliomas and progression-free survival in patients treated with DFMO-PCV chemotherapy," International Journal of Cancer, 121:(10): 2279-2283, 2010.
Linsalata et al., "Nutritional factors and polyamine metabolism in colorectal cancer," Nutrition, 24:382-389, 2008.
Lipkin, "New rodent models for studies of chemopreventive agents," J. Cell Biochem. Suppl., 28-29:144-7, 1997.
Love et al., "Randomized phase I chemoprevention dose-seeking study of alpha-difluoromethylornithine," J. Natl. Cancer Inst., 85:732-7, 1993.
Lozier et al., "Targeting ornithine decarboxylase reverses the LIN28/Let-7 axis and inhibits glycolytic metabolism in neuroblastoma," Oncotarget, 6:196-206, 2015.
Luk and Baylin, "Ornithine decarboxylase as a biologic marker in familial colonic polyposis," N. Engl. J. Med., 311(2):80-83, 1984.
Lupulescu, "Control of precancer cell transformation into cancer cells: its relevance to cancer prevention," Cancer Detect. Prev., 20(6):634-637, 1996.
Mackenzie et al., "Phospho-sulindac (OXT-328) combined with difluoromethylornithine prevents colon cancer in mice." Cancer prevention research 4.7 (2011): 1052-1060.
Martinez et al., "Pronounced reduction in adenoma recurrence associated with aspirin use and a polymorphism in the ornithine decarboxylase gene," Proc. Natl. Acad. Sci. USA, 100:7859-64, 2003.
Matsubara et al., "Association between high levels of ornithine decarboxylase activity and favorable prognosis in human colorectal carcinoma," Clinical Cancer Res., 1:665-71, 1995.
McGarrity et al., "Colonic polyamine content and ornithine decarboxylase activity as markers for adenomas," Cancer, 66:1539-1543, 1990.
McLaren et al., "Longitudinal assessment of air conduction audiograms in a phase III clinical trial of difluoromethylornithine and sulindac for prevention of sporadic colorectal adenomas," Cancer Prev. Res., 1(7):514-21, 2008.
Meyskens and Gerner, "Development of difluoromethylornithine as a chemoprevention agent for the management of colon cancer," J. Cell. Biochem., 22:126-131, 1995.

Meyskens et al., "Development of difluoromethylornithine (DFMO) as a chemoprevention agent," Clin. Cancer Res., 5:945-951, 1999.
Meyskens et al., "Difluoromethylornithine plus sulindac for the prevention of sporadic colorectal adenomas: a randomized placebo-controlled, double-blind trial," Cancer Prev. Res., 1(1):32-8, 2008.
Meyskens et al., "Dose de-escalation chemoprevention trial of alpha-difluoromethylornithine in patients with colon polyps," J. Natl. Cancer Inst., 86(15):1122-1130, 1994.
Meyskens et al., "Effect of alpha-difluoromethylornithine on rectal mucosal levels of polyamines in a randomized, double-blinded trial for colon cancer prevention," J. Natl. Cancer Inst., 90(16):1212-8, 1998.
Muscat et al., "Nonsteroidal antiinflammatory drugs and colorectal cancer," Cancer, 74:1847-1854, 1994.
Nishimura et al., "Independent roles of eIF5A and polyamines in cell proliferation," Biochem. J., 385:779-785, 2005.
O'Brien et al., "Differences in ornithine decarboxylase and androgen receptor allele frequencies among ethnic groups," Molec. Carcinog., 41(2):120-3, 2004.
Office Communication issued in European Patent Application No. 13786402.1, dated Dec. 15, 2016.
Office Communication issued in European Patent Application No. 13786402.1, dated Oct. 12, 2017.
Office Communication issued in U.S Appl. No. 14/483,999, dated Aug. 1, 2016.
Office Communication issued in U.S. Appl. No. 14/483,999, dated Apr. 6, 2017.
Office Communication issued in U.S. Appl. No. 14/483,999, dated Nov. 28, 2017.
Office Communication issued in U.S. Appl. No. 14/483,999, dated Jul. 26, 2018.
Pardali and Moustakas, "Actions of TGF-beta as tumor suppressor and pro-metastatic factor in human cancer," Biochimica et Biophysica Acta, 1775:21-62, 2007.
Pasricha et al., "The effects of sulindac on colorectal proliferation and apoptosis in familial adenomatous polyposis," Gastroenterology, 109:994-998, 1995.
Paz et al., "Plyamines are oncometabolites that regulate the LIN28/let-7 pathway in colorectal cancer cells," Molecular Carcinogensis, 2013.
PCT International Search Report and Written Opinion, issued in International Application No. PCT/US2013/067305, dated Jan. 2, 2014.
Peel et al., "Characterization of hereditary nonpolyposis colorectal cancer families from a population-based series of cases," J. Natl. Cancer Inst., 92:1517-22, 2000.
Pegg, "Recent advances in the biochemistry of polyamines in eukaryotes," Biochem., 234(2):249-262, 1986.
Piazza et al., "Antineoplastic drugs sulindac sulfide and sulfone inhibit cell growth by inducing apoptosis," Cancer Res., (55):3110-3116, 1995.
Piazza et al., "Apoptosis primarily accounts for the growth-inhibitory properties of sulindac metabolites and involves a mechanism that is independent of cyclooxygenase inhibition, cell cycle arrest, and p53 induction," Cancer Res., (57):2452-2459, 1997a.
Piazza et al., "Sulindac sulfone inhibits azoxymethane-induced colon carcinogenesis in rats without reducing prostaglandin levels," Cancer Res., (57):2909-2915, 1997b.
Pollard and Luckert, "Prevention and treatment of primary intestinal tumors in rats by piroxicam," Cancer Res., 49:6471-6473, 1989.
Porter et al., "Polyamine biosynthetic activity in normal and neoplastic human colorectal tissue," Cancer, 60:1275-1281, 1987.
Quemener et al., "Polyamine deprivation: a new tool in cancer treatment", Institute of Anticancer Research, 14:443-448, 1994.
Raj et al., "Role of dietary polyamines in a phase III clinical trial of difluoromethylornithine (DFMO) and sulindac for prevention of sporadic colorectal adenomas", British Journal of Cancer, 108(3):512-518, 2013.
Rao et al., "Chemoprevention of colon carcinogenesis by sulindac, a nonsteroidal anti-inflammatory agent," Cancer Res., (55):1464-1472, 1995.
Reddy et al., "Chemoprevention of colon carcinogenesis by concurrent administration of piroxicam, a nonsteroidal antiinflamma-

(56) References Cited

OTHER PUBLICATIONS tory drug with D,L-alpha-difluoromethylornithine, an ornithine decarboxylase inhibitor, in diet," Cancer Research, 50:2562-2568, 1990.
Reddy et al., "Dose-related inhibition of colon carcinogenesis by dietary piroxicam, a nonsteroidal antiinflammatory drug, during different stages of rat colon tumor development," Cancer Res., 47:5340-5346, 1987.
Rial et al., "Polyamines as mediators of APC-dependent intestinal carcinogenesis and cancer chemoprevention." Essays in biochemistry 46 (2009): 111-124.
Roberts and Wakefield, "The two faces of transforming growth factor beta in carcinogenesis," Proc. Natl. Acad. Sci. USA, 100:8621-3, 2003.
Rounbehler et al., "Targeting ornithine decarboxylase impairs development of MYCN-amplified neuroblastoma," Cancer Res., 69:547-553, 2009.
Saletta et al., "Molecular profiling of childhood cancer: Biomarkers and novel therapies," BBA Clinical, 1:59-77, 2014.
Samaha et al., "Modulation of apopotsosi by sulindac, curcumin, phenylethy1-3-methylcaffeate, and 6-phenylhexyl isothiocyanate, apoptotic index as a biomarker in colon cancer chemoprevention and promotion," Cancer Res., (57):1301-1305, 1997.
Samal et al., "AMXT-1501, a novel polyamine transport inhibitor, synergizes with DFMO in inhibiting neuroblastoma cell proliferation by targeting both ornithine decarboxylase and polyamine transport," Int. J. Cancer, 133:1323-1334, 2013.
Sausville and Burger, "Contributions of human tumor xenografts to anticancer drug development," Cancer Research 66.7 (2006): 3351-3354.
Seiler and Knodgen, "High-performance liquid chromatographic procedure for the simultaneous determination of the natural polyamines and their monoacetyl derivatives," J.Chromatogr., 221(2):227-235, 1980.
Seiler et al., "Endogenous and exogenous polyamines in support of tumor growth," Cancer Research, 50:5077-5083, 1990.
Sholler et al., [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr LB-179. doi: 10.1158/1538-7445.
Sholler et al., "A phase I trial of DFMO targeting polyamine addiction in patients with relapsed/refractory neuroblastoma." *PLoS One* 10.5 (2015): e0127246.
Silva et al., "Role of peripheral polyamines in the development of inflammatory pain," Biochemical Pharmacology, 82:269-277, 2011.
Simoneau et al., "Alpha-difluoromethylornithine and polyamine levels in the human prostate: results of a phase IIa trial," J. Natl. Cancer Inst., 93:57-9, 2001.
Simoneau et al., "The effect of difluoromethylornithine on decreasing prostate size and polyamines in men: results of a year-long phase IIb randomized placebo-controlled chemoprevention trial," Cancer Epidemiol. Biomarkers Prev., 17:292-9, 2008.
Singh and Reddy, "Molecular markers in chemoprevention of colon cancer Inhibition of expression of ras-p21 and p53 by sulindac during azoxymethane-induced colon carcinogenesis," Annals. NY Acad. Sci., (768):205-209, 1995.
Singh et al., "Bifidobacterium longum, a lactic acid-producing intestinal bacterium inhibits colon cancer and modulates the intermediate biomarkers of colon carcinogenesis," Carcinogenesis, 18:833-841, 1997.
Singh et al., "Modulation of azoxymethane-induced mutational activation of ras protooncogenes by chemopreventive agents in colon carcinogenesis," Carcinogenesis, (15):1317-1323, 1994.
Smithson et al., "Discovery of potent and selective inhibitors of Trypanosoma brucei ornithine decarboxylase," The Journal of Biological Chemistry, 265(22):16771-16781, 2010.
Soda et al., "Polyamine-rich food decreases age-associated pathology and mortality in aged mice," Experimental Gerontology, 44: 727-732, 2009.
Su et al., "Multiple intestinal neoplasia caused by a mutation in the murine homolog of the APC gene," Science, (256):668-670, 1992.
Tabib et al., "Role of polyamines in mediating malignant transformation and oncogene expression," Int. J. Biochem. Cell. Biol., 31:1289-1295, 1999.
Tempero et al., "Chemoprevention of mouse colon tumors with difluoromethylornithine during and after carcinogen treatment," Cancer Res., 49(21):5793-7, 1989.
Thomas and Thomas, "Polyamine metabolism and cancer," J. Cell Mol. Med., 7:113-26, 2003.
Thompson et al., "Inhibition of mammary carcinogenesis by sulfone metabolite of sulindac," J. Natl. Cancer Inst., (87):125-1260, 1995.
Thompson et al., "Levels of rectal mucosal polyamines and prostaglandin E2 predict ability of DFMO and sulindac to prevent colorectal adenoma," Gastroenterology, 139(3): 797-805, 2010.
Thompson, et al., "Sulfone metabolite of sulindac inhibits mammary carcinogenesis," Cancer Research, 57:267-271, 1997.
Vane and Botting, "Mechanism of action of anti-inflammatory drugs," Scand. J. Rheumatol., 25(Suppl. 102):9-21, 1996.
Vargas et al., "Dietary Polyamine intake and polyamines measured in urine," Nutrition and Cancer, 66(7): 1144-1153, 2014.
Visvanathan et al., "Association among an ornithine decarboxylase polymorphism, androgen receptor gene (CAG) repeat length and prostate cancer risk," J. Urol., 171(2 Pt 1):652-5, 2004.
Wallace and Caslake, "Polyamines and colon cancer," Eur J Gastroenterol Helatol., 13(9): 1033-1039, 2001.
Wallace, "The physiological role of the polyamines," Eur. J. Clin. Invest., 30:1-3, 2000.
Wang et al., "Mucosal polyamine measurements and colorectal cancer risk," J. Cell. Biochem., 63:252-257, 1996.
Zell et al., "Associations of a polymorphism in the ornithine decarboxylase gene with colorectal cancer survival," Clin. Cancer Res., 15(19):6208-16, 2009.
Zell et al., "Ornithine decarboxylase (Odc)-1 gene polymorphism effects on baseline tissue polyamine levels and adenoma recurrence in a randomized phase III adenoma prevention trial of DFMO + sulindac versus placebo," J. Clin. Oncol., 26(15S):Abstract 1502, 2008.
Zell et al., "Ornithine decarboxylase-1 polymorphism, chemoprevention with eflornithine and sulindac, and outcomes among colorectal adenoma patients," *J. Natl. Cancer Inst.*, 102:1513-1516, 2010.
Zell et al., "Risk and risk reduction involving arginine intake and meat consumption in colorectal tumorigenesis and survival," Intl. J. Cancer, 120:459-68, 2007.
Zell et al., "Risk of cardiovascular events in a randomized placebo-controlled, double-blind trial of difluoromethylornithine plus sulindac for the prevention of sporadic colorectal adenomas," Cancer Prev. Res., 2(3):209-12, 2009.
Zell et al., "Survival after colorectal cancer diagnosis is associated with colorectal cancer family history," Cancer Epidemiol. Biomarkers Prev., 17:3134-40, 2008.
Zeng et al., "New concept and clinical application of colorectal intraepithelial neoplasia and carcinoma." Zhonghua wai ke za zhi [Chinese journal of surgery] 45.7 (2007): 449-451.
Ziogas and Anton-Culver, "Validation of family history data in cancer family registries," Am. J. Prev. Med., 24:190-8, 2003.
Zoumas-Morse et al., "Development of a polyamine database for assessing dietary intake," J. Am. Diet. Assoc., 107:1024-1027, 2007.

\* cited by examiner

SEQUENCE LISTING

```
<160> NUMBER OF SEQ ID NOS: 2

<210> SEQ ID NO 1
<211> LENGTH: 8
<212> TYPE: DNA
<213> ORGANISM: Artificial Sequence
<220> FEATURE:
<223> OTHER INFORMATION: Synthetic LNA

<400> SEQUENCE: 1 actacctc                                                                 8

<210> SEQ ID NO 2
<211> LENGTH: 8
<212> TYPE: DNA
<213> ORGANISM: Artificial Sequence
<220> FEATURE:
<223> OTHER INFORMATION: Synthetic LNA

<400> SEQUENCE: 2 tcatacta                                                                 8
```

PREDICTIVE MARKERS FOR POLYAMINE INHIBITOR CANCER THERAPIES

The present application is a continuation of U.S. application Ser. No. 14/438,999, filed Apr. 28, 2015, as a national phase application under 35 U.S.C. § 371 of International Application No. PCT/US2013/067305, filed Oct. 29, 2013, which claims the priority benefit of U.S. provisional application No. 61/719,748, filed Oct. 29, 2012, the entire contents of each of which are incorporated herein by reference.

This invention was made with government support under grants P50 CA095060 and R01 CA123065 awarded by the National Institutes of Health. The government has certain rights in the invention.

BACKGROUND OF THE INVENTION

I. Field of the Invention

The present invention relates generally to the fields of cancer biology and medicine. More particularly, it concerns methods for the diagnosis, prevention, and treatment of carcinomas and risk factors thereof.

II. Description of Related Art

Cancer cells have the ability to co-opt multiple pathways to fulfill their increased requirement for specific metabolites (Vander Heiden, 2011). In particular, polyamine metabolism is a highly coordinated process that is associated with fundamental cellular activities, including proliferation and development (Gerner and Meyskens, 2004; Zhang et al., 2012). Polyamines are essential for both normal development and neoplastic growth in mammals, and elevated tissue levels of polyamines are frequently associated with cancers, including those of the colorectum, as a result of deregulated oncogenes and tumor suppressors (Gerner and Meyskens, 2004). Treatment of patients with agents that suppress colorectal polyamine contents dramatically reduces metachronous colorectal adenomas, which are precursors of colorectal cancers (CRC) (Meyskens et al., 2008). Furthermore, previous clinical cancer prevention trials demonstrated that polyamine metabolism is a tractable target to prevent risk of several epithelial cancers, including those of the colon, prostate and skin (Meyskens et al., 2008; Bailey et al., 2010; Simoneau et al., 2008). For example, the demonstrated marked efficacy of polyamine-inhibitory combination of long-term daily oral D,L-α-difluoromethylornithine (DFMO, eflornithine) and sulindac among colorectal adenoma (CRA) patients was recently demonstrated (Meyskens et al., 2008), however, treatment was associated with modest, subclinical ototoxicity (McLaren et al., 2008), and a greater number of cardiovascular events among patients with high baseline cardiovascular risk (Zell et al., 2009). Identifying genetic features that identify the suitability of a patient for a given preventative or curative treatment regime would be a major benefit.

SUMMARY OF THE INVENTION

Thus, in accordance with the present invention, there are provided methods of treatment, prevention, and/or diagnosis related to identifying a patient's expression level of a let-7 non-coding RNA, an HMGA2 protein, or a LIN28 protein.

In one aspect, there is provided a method for the preventative or curative treatment of cancer in a subject comprising (a) obtaining a result from a test that determines the expression of a let-7 non-coding RNA and (b) administering to the patient an effective amount of an inhibitor of ornithine decarboxylase (ODC) if the result from the test indicates that the subject exhibits a reduced expression level of a let-7 non-coding RNA, as compared to a level observed in a non-diseased subject. In one embodiment, obtaining a result may comprise receiving a report containing information of said levels. In another embodiment, obtaining a result may comprise providing a sample from said subject and assessing a let-7 non-coding RNA level in said sample. The test may comprise quantitative PCR. The sample may be blood or tissue, such as tumor tissue. The subject may be a human.

The cancer may be colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma. The cancer may be a carcinoma. The colorectal cancer may be is stage I, stage II, stage III, or stage IV. Administering may render an unresectable tumor resectable. The method may further comprise resecting said tumor.

The ODC inhibitor may be α-difluoromethylornithine (DFMO). The method may further comprise administering to said subject a non-steroidal anti-inflammatory drug (NSAID), such as a COX-2 inhibitor, a COX-2 selective inhibitor, sulindac, celecoxib, naproxen, diclofenac, or aspirin. The ODC inhibitor and/or NSAID may be is administered systemically, such as orally, intraarterially, or intravenously. The effective amount of DFMO may be 500 mg/day. The effective amount of DFMO may be from about 0.05 to about 5.0 g/m$^2$/day. The DFMO may be formulated as a hard or soft capsule, a tablet, or a liquid. The DFMO may be administered every 12 hours, or every 24 hours. The effective amount of sulindac may be from about 10 to about 1500 mg/day, from about 10 to about 400 mg/day, or about 150 mg/day. The ODC inhibitor may be administered prior to said NSAID, after said NSAID, or prior to and after said NSAID. The ODC inhibitor may be administered at the same time as said NSAID. The ODC inhibitor may be administered at least a second time. The NSAID may be administered at least a second time.

The method may further comprise (c) obtaining results from a test that determines the expression level of a let-7 non-coding RNA in a second cancer cell from said subject. The let-7 expression level in the second cancer cell may represent the let-7 expression level after the administration of at least one dose of the ODC inhibitor. The method may further comprise increasing the amount of said inhibitor administered to said subject if no or a small increase (e.g., less than 2-fold) in let-7 non-coding RNA is observed. The method may further comprise measuring LIN28 and/or HMGA2 in said cancer cell. The measuring of LIN28 and/or HMGA2 may comprise immunohistochemistry (e.g., quantitative IHC) or ELISA.

The method may further comprise (i) obtaining a result from a test that determines the patient's genotype at position +316 of at least one allele of a ODC1 gene promoter and (ii) administering to the patient a combined effective amount of α-difluoromethylornithine (DFMO) and a non-aspirin containing non-steroidal anti-inflammatory drug (NSAID) if the result from the test indicates that the patient's genotype at position +316 of at least one allele of the ODC1 gene promoter is G. The genotype identified at position +316 of both alleles of the patient's ODC1 gene promoters may be GG. The genotype identified at position +316 of both alleles of the patient's ODC1 gene promoters may be GA.

In another aspect, there is provided a method for the preventative or curative treatment of carcinoma in a subject comprising (a) obtaining a result from a test that determines the expression of a HMGA2 in a cancer cell from said subject and (b) administering to the patient an effective amount of an inhibitor of ornithine decarboxylase (ODC) if the result from the test indicates that the cancer cell exhibits elevated HMGA2 expression as compared to a level observed in a non-cancer cell. In one embodiment, the step of obtaining a result may comprise receiving a report containing information of said level. In another embodiment, obtaining a result may comprise providing a sample from said subject and assessing an HMGA2 level in said sample. The test may comprise quantitative immunohistochemistry (e.g., quantitative IHC) or ELISA. The sample may be blood or tissue, such as tumor tissue. The subject may be a human.

The cancer may be colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, and glioblastoma. The cancer may be a carcinoma. The colorectal cancer may be is stage I, stage II, stage III, or stage IV. Administering may render an unresectable tumor resectable. The method may further comprise resecting said tumor.

The ODC inhibitor may be α-difluoromethylornithine (DFMO). The method may further comprise administering to said subject a non-steroidal anti-inflammatory drug (NSAID), such as a COX-2 inhibitor, a COX-2 selective inhibitor, sulindac, celecoxib, or aspirin. The ODC inhibitor and/or NSAID may be is administered systemically, such as orally, intraarterially, or intravenously. The effective amount of DFMO may be 500 mg/day. The effective amount of DFMO may be from about 0.05 to about 5.0 g/m$^2$/day. The DFMO may be formulated as a hard or soft capsule, a tablet, or a liquid. The DFMO may be administered every 12 hours, or every 24 hours. The effective amount of sulindac may be from about 10 to about 1500 mg/day, from about 10 to about 400 mg/day, or about 150 mg/day. The inhibitor may be administered prior to said NSAID, after said NSAID, or prior to and after said NSAID. The inhibitor may be administered at the same time as said NSAID. The ODC inhibitor may be administered at least a second time. The NSAID may be administered at least a second time.

The method may further comprise (c) obtaining a result from a test that determines the expression of a HMGA2 in a second cancer cell from said subject. The HMGA2 level in the second cancer cell may represent the HMGA2 level after the administration of at least one dose of the ODC inhibitor. The method may further comprise increasing the amount of said inhibitor administered to said subject if no or a small decrease (e.g., less than 2 fold) in HMGA2 is observed. The method may further comprise measuring LIN28. The measuring of LIN28 and/or HMGA2 may comprise immunohistochemistry (e.g., quantitative IHC) or ELISA.

The method may further comprise (i) obtaining a result from a test that determines the patient's genotype at position +316 of at least one allele of a ODC1 gene promoter and (ii) administering to the patient a combined effective amount of α-difluoromethylornithine (DFMO) and a non-aspirin containing non-steroidal anti-inflammatory drug (NSAID) if the result from the test indicates that the patient's genotype at position +316 of at least one allele of the ODC1 gene promoter is G. The genotype identified at position +316 of both alleles of the patient's ODC1 gene promoters may be GG. The genotype identified at position +316 of both alleles of the patient's ODC1 gene promoters may be GA.

In still another aspect, there is provided a method for the preventative or curative treatment of cancer in a subject comprising (a) obtaining a result from a test that determines the expression level of LIN28 in a cancer cell from said subject and (b) administering to the patient an effective amount of an inhibitor of ornithine decarboxylase (ODC) if the result of the test indicates that the cancer cell exhibits elevated LIN28 expression as compared to a level observed in a non-cancer cell. In one embodiment, the step of obtaining a result may comprise receiving a report containing information of said level. In another embodiment, obtaining a result may comprise providing a sample from said subject and assessing a LIN28 level in said sample. The test may comprise immunohistochemistry or ELISA. The sample may be blood or tissue, such as tumor tissue. The subject may be a human.

The cancer may be colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, and glioblastoma. The cancer may be a carcinoma. The colorectal cancer may be is stage I, stage II, stage III, or stage IV. Administering may render an unresectable tumor resectable. The method may further comprise resecting said tumor.

The inhibitor may be α-difluoromethylornithine (DFMO). The method may further comprise administering to said subject a non-steroidal anti-inflammatory drug (NSAID), such as a COX-2 inhibitor, a COX-2 selective inhibitor, sulindac, celecoxib, or aspirin. The inhibitor and/or NSAID may be is administered systemically, such as orally, intraarterially or intravenously. The effective amount of DFMO may be 500 mg/day. The effective amount of DFMO may be from about 0.05 to about 5.0 g/m$^2$/day. The DFMO may be formulated as a hard or soft capsule, a tablet, or a liquid. The DFMO may be administered every 12 hours, or every 24 hours. The effective amount of sulindac may be from about 10 to about 1500 mg/day, from about 10 to about 400 mg/day, or about 150 mg/day. The inhibitor may be administered prior to said NSAID, after said NSAID, or prior to and after said NSAID. The inhibitor may be administered at the same time as said NSAID. The ODC inhibitor may be administered at least a second time. The NSAID may be administered at least a second time.

The method may further comprise (c) obtaining a result from a test that determines the expression of LIN28 in a second cancer cell from said subject. The LIN28 level in the second cancer cell may represent the LIN28 level after that administration of at least one dose of the ODC inhibitor. The method may further comprise increasing the amount of said inhibitor administered to said subject if no or a small decrease (e.g., less than 2 fold) in LIN28 is observed. The method may further comprise measuring HMGA2 in said cancer cell. The measuring of LIN28 and/or HMGA2 may comprise immunohistochemistry (e.g., quantitative IHC) or ELISA.

The method may further comprise (i) obtaining a result from a test that determines the patient's genotype at position +316 of at least one allele of a ODC1 gene promoter and (ii) administering to the patient a combined effective amount of α-difluoromethylornithine (DFMO) and a non-aspirin containing non-steroidal anti-inflammatory drug (NSAID) if the result from the test indicates that the patient's genotype at position +316 of at least one allele of the ODC1 gene promoter is G. The genotype identified at position +316 of both alleles of the patient's ODC1 gene promoters may be GG. The genotype identified at position +316 of both alleles of the patient's ODC1 gene promoters may be GA.

In yet other aspects, there are provided:

a method for predicting the efficacy of an anti-cancer therapy comprising an ornithine decarboxylase (ODC) inhibitor comprising assessing a cell or tissue let-7 level in a patient to be treated with said therapy, wherein a low cell or tissue let-7 level predicts a higher efficacy for said treatment;

a method for predicting the efficacy of an anti-cancer therapy comprising an ornithine decarboxylase (ODC) inhibitor comprising assessing a cell or tissue HMGA2 level in a patient to be treated with said therapy, wherein a high cell or tissue HMGA2 level predicts a higher efficacy for said treatment; and a method for predicting the efficacy of an anti-cancer therapy comprising an ornithine decarboxylase (ODC) inhibitor comprising assessing a cell or tissue LIN28 level in a patient to be treated with said therapy, wherein a high cell or tissue LIN28 level predicts a higher efficacy for said treatment.

In each of the foregoing aspects, the ornithine decarboxylase (ODC) inhibitor may be α-difluoromethylornithine (DFMO), and the therapy may further comprise an NSAID (e.g., a COX-2 inhibitor, a COX-2 selective inhibitor, sulindac, celecoxib, or aspirin). The preceding embodiments may also further comprise obtaining results of a test that determines said patient's genotype at position +316 of at least one allele of an ODC1 gene promoter, such as by receiving a report containing said genotype, taking a patient history that reveals said genotype, or testing to determine the nucleotide base at position +316 of one or both alleles of the ODC1 gene promoter of the patient. The patient may be a human. The cancer may be a carcinoma.

In another aspect, a method is provided for diagnosing a cancer or precancerous condition in a patient, the method comprising obtaining a sample from the patient; and determining an expression level of at least two markers selected from the group consisting of a let-7 non-coding RNA, a LIN28 protein, and a HMGA2 protein in the sample, wherein if the expression level of the let-7 non-coding RNA is decreased or the LIN28 protein or HMGA2 protein is increased in the sample relative to a reference level, then the patient is diagnosed as having cancer or a precancerous condition.

In one embodiment, the reference level may be a level observed in a non-disease subject. In one embodiment, the sample may be a blood sample, a tissue sample, or a tumor sample.

In one embodiment, determining the expression level of a let-7 non-coding RNA comprises performing quantitative PCR. In one embodiment, determining the expression level of a LIN28 protein or HMGA2 protein comprises performing quantitative immunohistochemistry. In one embodiment, determined the expression level of a LIN28 protein or HMGA2 protein comprises performed Western blotting. In one embodiment, the expression level of all three markers may be determined.

In one embodiment, the method may comprise providing a written report to the patient, a doctor, a hospital, or an insurance provider. In one embodiment, the method may comprise administering DFMO to the patient. The method may further comprise administering an NSAID to the patient (e.g., sulindac, celecoxib, naproxen, diclofenac, or aspirin).

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The term "effective," as that term is used in the specification and/or claims, means adequate to accomplish a desired, expected, or intended result.

As used herein, the term "$IC_{50}$" refers to an inhibitory dose that is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants, and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prevention" or "preventing" includes: (1) inhibiting the onset of a disease in a subject or patient who may be at risk and/or predisposed to the disease but does not yet experience or display any or all of the pathology or symptomatology of the disease, and/or (2) slowing the onset of the pathology or symptomatology of a disease in a subject or patient who may be at risk and/or predisposed to the disease but does not yet experience or display any or all of the pathology or symptomatology of the disease.

"Effective amount," "therapeutically effective amount," or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient who is experiencing or displaying the pathology or symptomatology of the disease (e.g., reversing the pathology and/or symptomatology), and/or (3) effecting any measurable decrease in a disease in a subject or patient who is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 1A, Measurements of intracellular polyamines, putrescine, spermidine, and spermine in cultures treated in the presence or absence of DFMO and/or putrescine for 96 h (N=4). The bars represent, from left to right, Control, Putrescine, DFMO, and Putrescine+DFMO. FIG. 1B, Cellular proliferation in the presence or absence of 5 mM DFMO. HCT116 cells were cultured with 50 µM putrescine in the presence or absence of 5 mM DFMO. Results are representative of three independent experiments. Closed squares, control. Closed circles, putrescine. Open circles, DFMO+putrescine. Open squares, DFMO. FIG. 1C, Expression of hsa-let-7i in colon cancer cells following DFMO treatment. Fold expression analyzed is relative to vehicle control using the comparative 2-Ct method (N=3). Black bars, Control. Gray bars, DFMO. FIG. 1D, Gene expression analysis of cells treated with or without 5 mM DFMO in the presence or absence of 50 µM putrescine for 72 h. Expression analyzed relative to vehicle control. Mean±s.d. are shown for all panels. ($P<0.01$; *$P<0.001$.).

FIG. 2A, Immunoblotting of protein extracts from HCT116 cells cultured with or without 5 mM DFMO. FIG. 1B, Relative luciferase activity in colon cancer cells transfected with reporter constructs containing a wild-type or mutated version of Hmga2 3' UTR, co-transfected with 25 nM anti-let-7 LNA or scramble LNA. Transfections were performed in both polyamine-rich and polyamine-depleted cells. Cultures were treated without (left panel) or with (right panel) 5 mM DFMO for 48 h prior to transfection. DFMO supplementation into normal media was continued for 72 h after opti-MEM based transfection. Data were normalized to cells transfected with wild-type Hmga2 reporter and mock transfected for LNAs. Data are representative of two independent experiments. White bars, wild-type Hmga2. Gray bars, mutant Hmga2. FIG. 2C, Western blot analysis of HMGA2 in cells with elevated polyamine levels compared to depleted polyamine cells transfected with anti-let-7 LNA or scramble LNA. Results are mean±SD. Immunoblots for each panel are representative of three independent experiments. Immunoblots were analyzed using densitometry and normalized to respective actin controls except for panel A, LIN28 putrescine supplementation experiment, which shows results of a single representative experiment that has been replicated. Error bars are SD (*$P<0.05$).

FIG. 3A, Immunoblots confirming knockdown of eIF5A1 and eIF5A2 using 25 nM Silencer Select inhibitors (Invitrogen). Inhibitors were transfected for 48 h into HCT116 cells stably expressing eIF5A2-V5-HIS C-terminal tag. Both the V5 transfected antigen and endogenous eIF5A levels were assessed in these immunoblots. FIG. 3B, Immunoblot of HMGA2 and LIN28 protein levels transfected with 25 nM scrambled LNAs or LNAs directed against eIF5A1 and eIF5A2. After 72 h, cells were harvested for protein. FIG. 3C, HCT116 cells were co-transfected with 25 nM anti-let-7 LNA and 25 nM eIF5A siRNAs. Actin shown as a loading control. Results are representative of three independent experiments. Immunoblots for panels A and B were analyzed using densitometry and normalized to the respective actin controls, panel C densitometry shows results of a single representative experiment, which has been replicated. Error bars are SD (*$P<0.05$).

DESCRIPTION OF ILLUSTRATIVE EMBODIMENTS

Figure 1A:
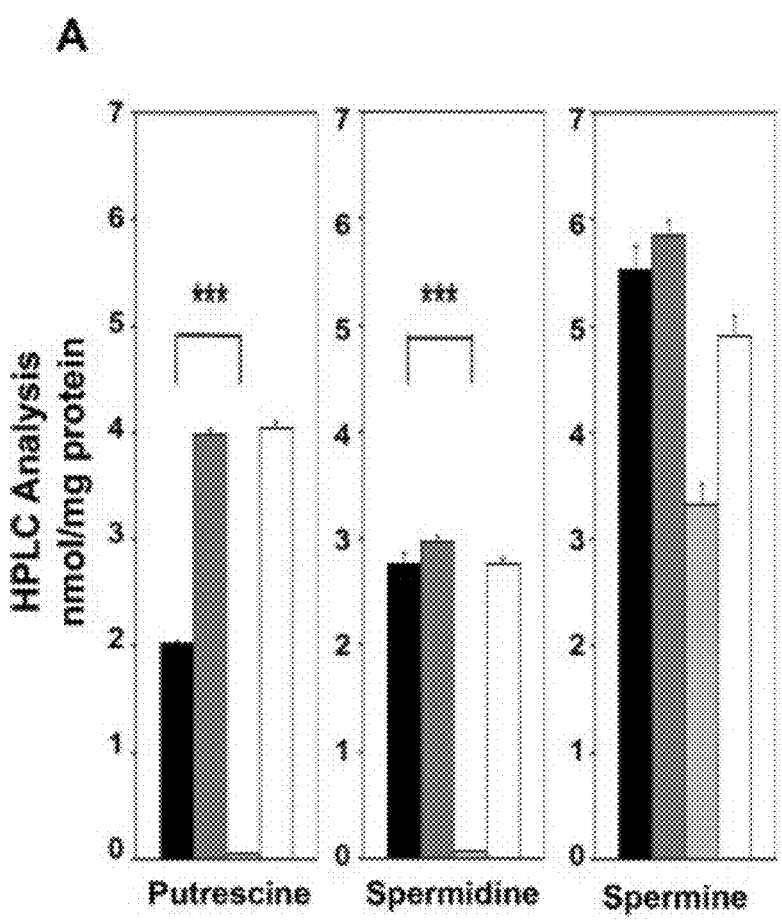
FIGS. 1A-D. Failure to maintain elevated levels of intracellular polyamines inhibits cellular proliferation and alters let-7 expression.

In several aspects, methods are provided that comprise predicting the suitability, efficacy, and/or dosage of anti-carcinoma combination therapies comprising ornithine decarboxylase (ODC) inhibitors and a non-steroidal anti-inflammatory drug. Said method is based at least in part on measuring the expression level of a let-7 miRNA, HMGA2 protein, or LIN28 protein in the patient's cancer.

I. POLYAMINE METABOLISM

Excess polyamine formation has long been implicated in epithelial carcinogenesis, particularly colorectal carcinogenesis. Polyamines are small ubiquitous molecules involved in various processes, including, for example, transcription, RNA stabilization, and ion channel gating (Wallace, 2000). Ornithine decarboxylase (ODC), the first enzyme in polyamine synthesis, is essential for normal development and tissue repair in mammals but is down-regulated in most adult tissues (Gerner and Meyskens, 2004). Multiple abnormalities in the control of polyamine metabolism and transport result in increased polyamine levels that can promote tumorigenesis in several tissues (Thomas and Thomas, 2003).

Polyamine metabolism is up-regulated in intestinal epithelial tissues of humans with familial adenomatous polyposis (FAP) (Giardiello et al., 1997), a syndrome associated with high risk of colon and other cancers. FAP may be caused by mutations in the adenomatous polyposis coli (APC) tumor suppressor gene, and APC signaling has been shown to regulate ODC expression in both human cells (Fultz and Gerner, 2002) and in a mouse model of FAP (Erdman et al., 1999).

Wild-type APC expression leads to decreased expression of ODC, while mutant APC leads to increased expression of ODC. The mechanism of APC-dependent regulation of ODC involves E-box transcription factors, including the transcriptional activator c-MYC and the transcriptional repressor MAD1 (Fultz and Gerner, 2002; Martinez et al., 2003). c-MYC was shown by others to regulate ODC transcription (Bellofernandez et al., 1993). Several genes involved in polyamine metabolism are essential genes for optimal growth in most organisms and are down-regulated in non-proliferating and/or adult cells and tissues (Gerner and Meyskens, 2004). The polyamines influence specific cellular phenotypes, in part, by affecting patterns of gene expression, as reviewed elsewhere (Childs et al., 2003).

As described below, a strategy involving inhibition of ODC activity (i.e., the rate-limiting enzyme of polyamine synthesis) and/or reduction of cellular polyamine levels has demonstrated remarkable efficacy in preventing recurrence of colorectal polyps in humans. Epidemiologic and experimental results demonstrate conditional regulation of polyamine homeostasis by genetic polymorphism in ODC, and suggest a model in which the +316 ODC SNP may be protective for colon adenoma recurrence and detrimental for survival after colon cancer diagnosis. This information may be used for determining colon cancer prognosis. Identifying patients at increased risk for cancer progression/recurrence allows for the institution of early implementation of tertiary prevention management strategies. Additionally, this research may be used to identify high-risk but otherwise optimally-treated locoregional colorectal cancer patients that would benefit from tertiary cancer prevention therapies.

Depending on a patient's diet, the problems associated with excess polyamine may be compounded by the fact that polyamines, e.g., putrescine, are present in many common foods, such as orange juice, which contains approximately 400 ppm putrescine. In this regard, a high polyamine diet is contraindicated, and for some of the embodiments provided herein, such a diet is to be avoided.

Polyamines are oncometabolites that regulate the expression of the microRNA-binding protein LIN28 and several microRNAs, including let-7, which are key regulators of development and proliferation (Viswanthan et al., 2008; 2010). Polyamine-depletion caused by treatment with difluoromethylornithine (DFMO) suppresses expression of both LIN28 and HMGA2, which are both known let-7-regulated proteins. Neutralizing the let-7 family using locked nucleic acid (LNA) antisense oligonucleotides (Obad et al., 2011) rescues HMGA2 expression in the presence of DFMO. Knockdown of the polyamine-modified eukaryotic translation initiation factor 5A (eIF5A) isoforms 1 and 2 suppresses both LIN28 and HMGA2 expression. Without being bound by theory, these findings indicate that polyamines regulate proliferation and pluripotency-associated factors, such as HMGA2, in part via eIF5A and microRNA-mediated translational repression. Applying these observations to clinical settings better identifies patient subsets that will benefit from polyamine-directed therapies, allowing for tailored therapeutic intervention based on the ability of the subject to respond to such therapies.

II. FAMILIAL ADENOMATOUS POLYPOSIS

Familial adenomatous polyposis (FAP), an inherited polyposis syndrome, may be the result of a germ-line mutation in the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age for diagnosis of sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, GI obstruction, and death. A combination therapy of DFMO and sulindac is effective in reducing adenomas in these mice (U.S. Pat. No. 6,258,845; Gerner and Meyskens, 2004).

III. NEUROBLASTOMA

The results provided herein also have relevance to diseases other than colorectal carcinoma that exhibit dysregulated let-7 expression, such as neuroblastoma (Buechner et al., 2011). Indeed, preclinical data indicates that polyamine targeted therapies may be effective against neuroblastoma (Hogarty et al., 2008). In fact, DFMO has shown single agent cytotoxicity against neuroblastoma cell lines (Samal et al., 2013, which is incorporated herein by reference in its entirety). Specifically, DFMO was found to have $IC_{50}$ concentrations between 20.76 and 33.3 mM against three neuroblastoma cell lines (SMS-KCNR, SH-SY5Y, and BE(2)-C) after 48 h of treatment. In some embodiments, the methods provided herein may be used for treating patients with neuroblastoma.

IV. ORNITHINE DECARBOXYLASE-1 POLYMORPHISM

Activity of ornithine decarboxylase (ODC), the first enzyme in polyamine synthesis, is required for normal growth and is elevated in many cancers, including colorectal cancer. Associations of the +316 ODC single nucleotide polymorphism (SNP) with colorectal cancer (CRC)-specific survival among CRC cases were examined and its functional significance in colon cancer cells was investigated.

A single nucleotide polymorphism (SNP) in intron 1 of the human ODC1 gene affects ODC1 transcription (Guo et al., 2000), and has been investigated as a genetic marker for colorectal adenoma (CRA) risk (Martinez et al., 2003; Barry et al., 2006; Hubner et al., 2008). The reported minor A allele frequency is approximately 25% and, despite differences across race/ethnicity, ODC1 genotype distribution is in Hardy-Weinberg equilibrium within each race (O'Brien et al., 2004; Zell et al., 2009a). Individuals homozygous for the ODC1 minor A allele have reduced risk of adenoma recurrence compared to those with the major G allele (Martinez et al., 2003; Hubner et al., 2008). Furthermore, the ODC1 A allele (AA or GA genotype, but not GG genotype) and reported aspirin usage have been associated with reduced colon polyp recurrence (Martinez et al., 2003; Barry et al., 2006; Hubner et al., 2008), and a statistically significant 50% reduced risk of advanced adenomas (Barry et al., 2006).

The ODC allele-specific binding of E-box transcription factors was investigated and the functional significance of the +316 ODC SNP, located between two E-boxes (E-box 2 and 3), was evaluated. HT29 cells were found to contain at least one ODC A allele. HCT116 cells were found to contain only ODC G alleles.

Expression of specific E-box binding proteins, including the transcriptional activator c-MYC and several transcriptional repressors in HT29 and HCT116 cells (e.g. MAD1 and MAD4), was analyzed. Chromatin immunoprecipitation (CHIP) analysis of the region surrounding +316 of the ODC promoter was conducted using antibodies directed against these proteins. These results indicated that c-MYC, MAD1, and MAD4 binding to the ODC SNP region was 4-14 times greater in HT29 cells, which contained one ODC A allele, compared to HCT116 cells, which contained only ODC G alleles.

ODC allele-specific promoter activity was assessed. c-MYC expression had the greatest stimulatory effect on promoters containing three consensus E-boxes and the ODC A allele. Deletion of the upstream E-box reduced promoter activity, but c-MYC expression continued to stimulate this activity. Substitution of a G for the A at the +316 SNP position reduced the ability of c-MYC to stimulate promoter activity even with an intact 5' flanking consensus E-box. Mutation of the 5' flanking consensus E-box in combination with the ODC G allele further reduced promoter activity.

When MAD1, rather than c-MYC, was co-transfected with the ODC allele-specific promoter reporters, the repressor was only able to reduce the activity of the ODC promoter that contained all three E-boxes and the wild-type +316 A allele. Deletion of the upstream E-box significantly reduced the effect of MAD1 on ODC promoter activity. Substitution of G for A at the +316 position rendered promoters containing either two or three E-boxes unresponsive to MAD1 suppression.

V. DIFLUOROMETHYLORNITHINE (DFMO)

DFMO, also known as eflornithine, has the following chemical designation: 2-(difluoromethyl)-dt-ornithine. It is an enzyme-activated irreversible inhibitor of ornithine decarboxylase (ODC), the rate-limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

DFMO decreases APC-dependent intestinal tumorigenesis in mice (Erdman et al., 1999). Oral DFMO administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). Of note, DFMO in combination with the non-steroidal anti-inflammatory drug (NSAID) sulindac markedly lowered adenoma recurrence rates among individuals with colonic adenomas when compared to placebo treatment in a randomized clinical trial (Meyskens et al., 2008).

DFMO was originally synthesized by Centre de Recherche Merrell, Strasbourg. Current FDA approvals include
  African sleeping sickness. High dose systemic IV dosage form. Not marketed (Sanofi/WHO).
  Hirsutis (androgen-induced excess hair growth) topical dosage form.
No oral formulations are currently approved.

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO was capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally or parenterally.

DFMO can potentially be given continuously with significant anti-tumor effects. This drug is relatively non-toxic at low doses of 0.4 $g/m^2/day$ to humans while producing inhibition of putrescine synthesis in tumors. Studies in a rat-tumor model demonstrate that DFMO infusion can produce a 90% decrease in tumor putrescine levels without suppressing peripheral platelet counts.

Side effects observed with DFMO include effects on hearing at high doses of 4 $g/m^2/day$ that resolve when it is discontinued. These effects on hearing are not observed at lower doses of 0.4 $g/m^2/day$ when administered for up to one year (Meyskens et al., 1994). In addition a few cases of dizziness/vertigo are seen that resolve when the drug is stopped. Thrombocytopenia has been reported predominantly in studies using high "therapeutic" doses of DFMO (>1.0 $g/m^2/day$) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

A phase III clinical trial assessed the recurrence of adenomatous polyps after treatment for 36 months with difluoromethylornithine (DFMO) plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies. There was no significant difference in the proportion of subjects in the DFMO plus sulindac group who experienced clinically significant hearing loss compared with the placebo group. The estimated attributable risk of ototoxicity from exposure to the drug is 8.4%. There is a <2 dB difference in mean threshold for patients treated with DFMO plus sulindac compared with those treated with placebo. The results of this study are discussed in greater detail in McLaren et al. (2008), which is incorporated herein by reference in its entirety.

VI. NSAIDS

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function (AMA Drug Evaluations Annual, 1994).

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, are a function of their ability to inhibit prostaglandin synthesis (reviewed in DuBois et al., 1996; Lupulescu, 1996; Vane and Botting, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin E2 (PGE2) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

A. Aspirin

Aspirin, also known as acetylsalicylic acid, is a salicylate drug, often used as an analgesic to relieve minor aches and pains, as an antipyretic to reduce fever, and as an anti-inflammatory medication. Aspirin was first isolated by Felix Hoffmann, a chemist with the German company Bayer in 1897. Salicylic acid, the main metabolite of aspirin, is an integral part of human and animal metabolism. While in humans much of it is attributable to diet, a substantial part is synthesized endogenously. Today, aspirin is one of the most widely used medications in the world, with an estimated 40,000 tons of it being consumed each year. In countries where Aspirin is a registered trademark owned by Bayer, the generic term is acetylsalicylic acid (ASA).

Aspirin also has an antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. It has also been established that low doses of aspirin may be given immediately after a heart attack to reduce the risk of another heart attack or of the death of cardiac tissue. Aspirin may be effective at preventing certain types of cancer, particularly colorectal cancer.

The main undesirable side effects of aspirin taken by mouth are gastrointestinal ulcers, stomach bleeding, and tinnitus, especially in higher doses. In children and adolescents, aspirin is no longer indicated to control flu-like symptoms or the symptoms of chickenpox or other viral illnesses, because of the risk of Reye's syndrome.

Aspirin is part of a group of medications called nonsteroidal anti-inflammatory drugs (NSAIDs), but differs from most other NSAIDS in the mechanism of action. Though it, and others in its group called the salicylates, have similar effects (antipyretic, anti-inflammatory, analgesic) to the other NSAIDs and inhibit the same enzyme cyclooxygenase, aspirin (but not the other salicylates) does so in an irreversible manner and, unlike others, affects more the COX-1 variant than the COX-2 variant of the enzyme.

B. Sulindac, Sulindac Sulfone, and Sulindac Sulfide

Sulindac is a non-steroidal, anti-inflammatory indene derivative with the following chemical designation: (Z)-5-fluoro-2-methyl-1-((4 (methyl sulfinyl)phenyl)methylene) 1H-indene-3-acetic acid (Physician's Desk Reference, 1999). The sulfinyl moiety is converted in vivo by reversible reduction to a sulfide metabolite and by irreversible oxidation to a sulfone metabolite (exisulind). See U.S. Pat. No. 6,258,845, which is incorporated herein by reference in its entirety. Sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 h in fasting patients and 3-4 h when administered with food. The mean half-life of sulindac is 7.8 h. The mean half-life of the sulfide metabolite is 16.4 h. U.S. Pat. Nos. 3,647,858 and 3,654,349 cover preparations of sulindac, and both are incorporate by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and anti-inflammatory effects exerted by sulindac (400 mg per day) are comparable to those achieved by aspirin (4 g per day), ibuprofen (1200 mg per day), indometacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity, such as bleeding, ulceration, and perforation.

The potential use of sulindac for chemoprevention of cancers, and in particular colorectal polyps, has been well studied. Two recent U.S. Pat. Nos. 5,814,625 and 5,843,929, detail potential chemopreventive uses of sulindac in humans. Both patents are incorporated herein in their entireties. Doses of sulindac claimed in U.S. Pat. No. 5,814,625 range from 10 mg to 1500 mg per day, with preferred doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention. Sulindac has been shown to produce regression of adenomas in Familial Adenomatous Polyposis (FAP) patients (Muscat et al., 1994), although at least one study in sporadic adenomas has shown no such effect (Ladenheim et al., 1995). Sulindac and its sulfone metabolite exisulind have been tested and continue to be tested clinically for the prevention and treatment of several cancer types.

C. Piroxicam

Piroxicam is a non-steroidal anti-inflammatory agent that is well established in the treatment of rheumatoid arthritis and osteoarthritis with the following chemical designation: 4-hydroxy-2-methyl-N-2-pyridyl-2H-1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

Piroxicam has been shown to be effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Reddy et al., 1990). In one study, administration of DFMO or piroxicam to AOM-treated rats reduced the number of tumors harboring Ki-ras mutations from 90% to 36% and 25%, respectively (Singh et al., 1994). Both agents also reduced the amount of biochemically active p21 ras in existing tumors.

D. Celecoxib

Celecoxib is a non-steroidal anti-inflammatory agent that is well established in the treatment of osteoarthritis, rheumatoid arthritis, acute pain, ankylosing spondylitis, and to reduce the number of colon and rectal polyps in patients with FAP with the following chemical designation: 4-[5-(4-Methylphenyl)-3-(trifluoromethyl)pyrazol-1-yl]benzenesulfonamide. Celecoxib is marketed under the brand names Celebrex, Celebra, and Onsenal by Pfizer. Celecoxib is a selective COX-2 inhibitor. Side effects of celecoxib include a 30% increase in rates of heart and blood vessel disease. Additionally, the risk of gastrointestinal side effects are greater than 80%.

E. Combinations of NSAIDs

Combinations of various NSAIDs are also used for various purposes. By using lower doses of two or more NSAIDs, it is possible to reduce the side effects or toxicities associated with higher doses of individual NSAIDs. For example, in some embodiments, sulindac may be used together with celecoxib. In some embodiments, the one or both of the NSAIDS are selective COX-2 inhibitors. Examples of NSAIDS that might be used either alone or in combination include, but are not limited to, the following: ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib rofecoxib valdecoxib parecoxib, lumiracoxib, or etoricoxib.

VII. EFLORNITHINE/SULINDAC COMBINATION THERAPY

Preclinical studies of chemoprevention drugs given in combination at low doses show remarkable efficacy in preventing adenomas with little additional toxicities, suggesting a strategy to improve risk to benefit ratios for preventing recurrent adenomas.

As noted above, the Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice (U.S. Pat. No. 6,258,845; Gerner and Meyskens, 2004).

In addition, a statistically significant interaction was detected for ODC1 genotype and treatment in a full model for adenoma recurrence, such that the pattern of adenoma recurrence among placebo patients was: GG 50%, GA 35%, AA 29% versus eflornithine/sulindac patients: GG 11%, GA 14%, AA 57%. The adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). These results demonstrate that ODC1 A allele carriers differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes.

VIII. EFFICACY OF POLYAMINE-INHIBITORY THERAPY BASED ON PATIENT PROFILE

The efficacy of a polyamine-inhibitory combination of long-term daily oral D,L-α-difluoromethylornithine (DFMO, eflornithine) and sulindac among CRA patients was demonstrated (Meyskens et al., 2008), but treatment was associated with modest, subclinical ototoxicity (McLaren et al., 2008), and a greater number of cardiovascular events among patients with high baseline cardiovascular risk (Zell et al., 2009b). However, a patient's ODC1 genotype differentially affects adenoma recurrence, tissue polyamine responses, and toxicity profiles after eflornithine and sulindac treatment compared to placebo.

Patients (n=375) with a history of resected (> or =3 mm) adenomas were randomly assigned to receive oral DFMO (500 mg) and sulindac (150 mg) once daily or matched placebos for 36 months, stratified by use of low-dose aspirin (81 mg) at baseline and clinical site. This study involved analysis of patient data from a multicenter phase III colon adenoma prevention trial. Comparing the outcome in patients receiving placebos to those receiving active intervention, (a) the recurrence of one or more adenomas was 41.1% and 12.3%; (b) 8.5% vs. 0.7% had one or more advanced adenomas; and (c) 17 (13.2%) patients vs. 1 patient had multiple adenomas (>1) at the final colonoscopy. Therefore, recurrent adenomatous polyps can be markedly reduced by a combination of low oral doses of DFMO and sulindac. The details of this study are discussed in Meyskens et al. (2008), which is incorporated herein by reference in its entirety.

A. ODC1 Genotype Distribution

A total of 440 colorectal cancer (CRC) cases identified from the UC Irvine CRC gene-environment study were used in a case-only analysis. ODC1+316 genotype distribution among all CRC cases was 53% GG, 41% GA, and 7% AA. ODC +316 genotype distribution was similar among CRC cases with and without a family history. There were no significant differences in ODC1 genotype distribution by age, gender, family history, site within the colorectum, histology, or tumor grade. ODC1 genotype distribution did not significantly differ by stage at diagnosis: stage I (49% GG, 42% GA, 8% AA), stage II (56% GG, 38% GA, 6% AA), stage III (51% GG, 43% GA, 6% AA), stage IV (59% GG, 37% GA, 4% AA). ODC1 genotype distribution by ethnicity revealed significant differences: Caucasian (382 cases: 53% GG, 41% GA, 6% AA, minor A allele frequency=26%), African-American (7 cases: 71% GG, 29% GA, 0% AA, minor A allele frequency=15%), Hispanics (21 cases: 57% GG, 43% GA, 0% AA, minor A allele frequency=21%), and Asians (27 cases: 33% GG, 41% GA, 26% AA, minor A allele frequency=46%). However, within each race ODC1 genotype distribution was in Hardy-Weinberg equilibrium.

B. Adenoma Recurrence

ODC1 genotype distribution was: 126 GG (55%), 87 GA (38%), and 15 AA (7%). A statistically significant interaction was detected for ODC1 genotype and treatment in the full model for adenoma recurrence, such that the pattern of adenoma recurrence among placebo patients was: GG 50%, GA 35%, AA 29% versus eflornithine/sulindac patients: GG 11%, GA 14%, AA 57%. ODC1 genotype was not significantly associated with a tissue putrescine response or spermidine:spermine ratio response. There were no significant associations between treatment and ODC1 genotype group with regard to cardiovascular or gastrointestinal adverse events.

The adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). ODC1 genotype distribution was similar to that reported in prior aspirin-based trials (Martinez et al., 2003; Barry et al., 2006; Hubner et al., 2008), and the A allele was associated with a non-significant lower recurrent adenoma risk in the placebo group consistent with previous reports (Martinez et al., 2003; Hubner et al., 2008). These results demonstrate that ODC1 A allele carriers differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes.

C. Survival Analysis

Of the 440 CRC cases, 138 (31%) were deceased at the time of analysis. Sixty-four (46%) deaths occurred in cases carrying the GG genotype, compared to 74 (54%) deaths in cases with the AA/AG genotypes. CRC-specific survival analysis by stage revealed that significantly different survival differences were not observed for AJCC stage I, II, or IV CRC. However, among cases with stage III CRC the ODC1 GG genotype was associated with improved 10-year CRC-specific survival. Among colon cancer cases, a statistically significant CRC-specific survival benefit was observed for those with ODC1 GG genotype compared to ODC1 GA/AA; this was not observed for rectal cancer cases.

Among all CRC cases, the CRC-specific survival estimates based on ODC1 genotype after adjustment for age (years), gender, ethnicity, family history of CRC, TNM stage at diagnosis, tumor site within the colon, histologic subtype, treatment with surgery, radiation therapy, and chemotherapy were a follows: ODC GG hazards ratio (HR)=1.00 (referent), ODC GA HR=1.73, and ODC AA genotype HR=1.73. Among colon cases only, CRC-specific survival analysis revealed that the ODCJ+316 SNP was an independent predictor of CRC-specific survival, after adjustment for the above clinical variables. Among rectal cancer cases, CRC-specific survival analysis revealed that the ODCJ+316 SNP was not an independent predictor of CRC-specific survival after adjustment for the aforementioned clinical variables.

Based on this population-based analysis of colorectal cancer cases, the +316 ODC1 SNP was associated with colorectal cancer specific survival among colon cancer cases. A statistically significant increased risk of CRC-specific mortality was observed with each additional ODC1 A allele among colon cancer cases, i.e., from ODC1 GG to GA to AA, after adjustment for age, gender, ethnicity, tumor stage, family history of CRC, tumor site, histology, treatment with surgery, radiation therapy, and chemotherapy.

D. Allele Specific Regulation of Transcription Factors

In colon cancer epithelial cells, the ODCJ+316 SNP is functionally significant, as evidenced by increased binding of E-box transcription factors to promoter elements containing A, compared to G, alleles. Both the activator c-MYC and the repressor MAD1 show greater effects on promoter activity in reporter elements containing A versus G alleles. These results suggest allele-specific regulation of ODC1 expression by E-box transcription factors. ODC protein enzyme activity is not affected by the ODC1 +316 SNP genotype.

In colon cells, conditional expression of wild type APC, a gene expressed in normal colonic mucosa, suppresses c-MYC, and increases MAD1, expression (Fultz and Gerner, 2002). Further, wild-type APC can regulate ODC1 promoter activity in a manner dependent on the +316 SNP (Martinez et al., 2003). Wild-type APC is expressed in the apparently normal colonic mucosa of individuals not afflicted with FAP, while the majority of sporadic colon adenomas show evidence of mutated or deleted APC (Iwamoto et al., 2000). MYC is expressed at low levels in normal intestinal mucosa but is increased in intestinal adenomas of APC$^{Min/+}$ mice. Conditional knockout of intestinal epithelial MYC expression suppresses intestinal tumorigenesis in APC$^{Min/+}$ mice (Ignatenko et al., 2006). Previous work (Martinez et al., 2003; Hubner et al., 2008) has demonstrated a protective role for the ODC1 A allele, especially in aspirin users, against recurrence of colon polyps in clinical prevention trials. However, in the population-based study, the ODC1 A allele was associated with poor survival. This apparent contradiction may be explained by the idea that both E-box activators and repressors bind the ODC1 A allele selectively. The transition from normal epithelium, expressing E-box repressors, to neoplastic epithelium may be retarded in individuals with ODC1 A alleles. This effect may result from suppression of polyamine synthesis. However, if the transformed epithelium begins to express E-box activators (such as c-MYC), then cancer progression may be more likely to occur in individuals with the ODC1 A genotype. The results for risk of colon cancer-specific mortality are consistent with those showing that risk of prostate cancer may be associated with the ODC1 A allele among specific individuals as the result of gene environment interactions (O'Brien et al., 2004; Viswanathan et al., 2004). Such colon cancer progression could be due to enhanced polyamine synthesis, as has been demonstrated already for prostate cancer (Simoneau et al., 2008).

This finding that a factor, such as the ODC1 SNP, may have both promoting and inhibiting effects on carcinogenesis is not unique. For example, transforming growth factor-beta (TGF-β) has diverse roles in carcinogenesis and cancer progression (Derynck et al., 2001; Pardali and Moustakas, 2007; Roberts and Wakefield, 2003). TGF-β in untransformed cells inhibits cell proliferation and induces apoptosis. Yet, it is overexpressed in all human tumors and is associated with late cancer progression, specifically tumor invasion and metastasis. A single study reporting ODC activity in human colorectal tumors demonstrated that high levels of ODC expression was significantly associated with improved survival (Matsubara et al., 1995). This suggests that, although ODC overexpression promotes the formation of human colorectal adenomas, it is possible that in established lesions, ODC overexpression causes enhanced proliferation and is associated with improved response to anti-proliferative treatments. However, that study did not include stratification by ODC genotype, so it is not known if these effects are independent of ODC genotype.

E. Summary

In summary, a statistically significant interaction was detected for ODC1 genotype and treatment in the full model for adenoma recurrence (P=0.021), such that the pattern of adenoma recurrence among placebo patients was: GG 50%, GA 35%, AA 29% versus eflornithine/sulindac patients: GG 11%, GA 14%, AA 57%. The adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). These results demonstrate that ODC1 A allele carriers differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes. The details of this study are discussed in U.S. Pat. No. 8,329,636, which is incorporated herein by reference in its entirety.

IX. MARKER ANALYSIS

The present invention describes, in one aspect, the identification of a series of marker that are surrogates for polyamine expression. Indeed, they appear to be downstream effectors that are tied more closely to the pathologic mechanism in cancer cells than even the polyamines themselves. As such, these present the opportunity to more accurately predict subjects that will be responsive to polyamine-modulating drugs, and to assess and tailor such therapies in a "real time" approach.

A. Let-7 Family Non-Coding RNAs

The let-7 microRNA precursor was identified from a study of developmental timing in *C. elegans* and was later shown to be part of a much larger class of non-coding RNAs termed microRNAs. The human miR-98 microRNA precursor is a let-7 family member. Let-7 miRNAs have now been predicted or experimentally confirmed in a wide range of species. miRNAs are initially transcribed in long transcripts (up to several hundred nucleotides) called primary miRNAs (pri-miRNAs), which are processed in the nucleus by Drosha and Pasha to hairpin structures of about ~70 nucleotide. These precursors (pre-miRNAs) are exported to the cytoplasm by exportin5, where they are subsequently processed by the enzyme Dicer to a ~22 nucleotide mature miRNA. The involvement of Dicer in miRNA processing demonstrates a relationship with the phenomenon of RNA interference.

In human genome, the cluster let-7a-1/let-7f-1/let-7d is inside the region B at 9q22.3, with the defining marker D9S280-D9S1809. One minimal LOH (loss of heterozygosity) region, between loci D11S1345-D11S1316, contains the cluster miR-125b1/let-7a-2/miR-100. The cluster miR-99a/let-7c/miR-125b-2 is in a 21p11.1 region of HD (homozygous deletions). The cluster let-7g/miR-135-1 is in region 3 at 3p21.1-p21.2.

The lethal-7 (let-7) gene was first discovered in the nematode as a key developmental regulator and became one of the first two known microRNAs (the other being lin-4). Soon, let-7 was found in fruit flies and was identified as the first known human miRNA by a BLAST (basic local alignment search tool) search. The mature form of let-7 family members is highly conserved across species. In *C. elegans*, the let-7 family consists of genes encoding nine miRNAs sharing the same seed sequence. Among them, let-7, mir-84, mir-48 and mir-241 are involved in *C. elegans* heterochronic pathway, sequentially controlling developmental timing of larva transitions. Most animals with loss-of-function let-7 mutation burst through their vulvas and die, and therefore the mutant is lethal (let). The mutants of other let-7 family members have a radio-resistant phenotype in vulval cells, which may be related to their ability to repress RAS. There is only one single let-7 gene in the *Drosophila* genome, which has the identical mature sequence to the one in *C. elegans*. The role of let-7 has been demonstrated in regulating the timing of neuromuscular junction formation in the abdomen and cell-cycle in the wing. Furthermore, the expression of pri-, pre-, and mature let-7 have the same rhythmic pattern with the hormone pulse before each cuticular molt in *Drosophila*.

The let-7 family has a lot more members in vertebrates than in *C. elegans* and *Drosophila*. And the sequences, expression timing, as well as genomic clustering of these miRNAs members are all conserved across species. The direct role of the let-7 family in vertebrate development has not been clearly shown as in less complex organisms, yet the expression pattern of the let-7 family is indeed temporal during developmental processes. Given that the expression levels of let-7 members are significantly lower in human cancers and cancer stem cells, the major function of let-7 genes may be to promote terminal differentiation in development and tumor suppression.

Although the levels of mature let-7 members are undetectable in undifferentiated cells, the primary transcripts and the hairpin precursors of let-7 are present in these cells, which indicates that mature let-7 miRNAs may be regulated in a post-transcriptional manner.

As one of the four genes involved in induced pluripotent stem (iPS) cell reprogramming, LIN28 expression is reciprocal to that of mature let-7. LIN28 selectively binds the primary and precursor forms of let-7, and inhibits the processing of pri-let-7 to form the hairpin precursor. This binding is facilitated by the conserved loop sequence of primary let-7 family members and RNA-binding domains of LIN28 proteins. On the other hand, let-7 miRNAs in mammals have been shown to regulate LIN28, which implies that let-7 might enhance its own level by repressing LIN28, its negative regulator.

Expression of let-7 members is controlled by MYC binding to their promoters. The levels of let-7 have been reported to decrease in models of MYC-mediated tumorigenesis, and to increase when MYC is inhibited by chemicals. However, there are let-7-binding sites in MYC 3' UTR according to bioinformatic analysis, and let-7 overexpression in cell culture decreased MYC mRNA levels. Therefore, there is a double-negative feedback loop between MYC and let-7. Furthermore, let-7 could lead to IMP1 (insulin-like growth factor II mRNA-binding protein) depletion, which destabilizes MYC mRNA, thus forming an indirect regulatory pathway.

Let-7 has been demonstrated to be a direct regulator of RAS expression in human cells. All the three RAS genes in human, K-, N-, and H-, have the predicted let-7 binding sequences in their 3' UTRs. In lung cancer patient samples, expression of RAS and let-7 showed reciprocal pattern, which has low let-7 and high RAS in cancerous cells, and high let-7 and low RAS in normal cells. Another oncogene, high mobility group A2 (HMGA2), has also been identified as a target of let-7. Let-7 directly inhibits HMGA2 by binding to its 3' UTR. Removal of the let-7 binding site by 3' UTR deletion caused overexpression of HMGA2 and tumor formation. MYC is also considered to be an oncogenic target of let-7.

Microarray analyses revealed many genes regulating cell cycle and cell proliferation that are responsive to alteration of let-7 levels, including cyclin A2, CDC34, Aurora A and B kinases (STK6 and STK12), E2F5, and CDK8, among others. Subsequent experiments confirmed the direct effects of some of these genes, such as CDC25A and CDK6. Let-7 also inhibits several components of DNA replication machinery, transcription factors, even some tumor suppressor genes and checkpoint regulators. Apoptosis is regulated by let-7 as well, through Casp3, Bcl2, Map3k1 and Cdk5 modulation.

Let-7 has been implicated in post-transcriptional control of innate immune responses to pathogenic agents. Macrophages stimulated with live bacteria or purified microbial components down-regulate the expression of several members of the let-7 miRNA family to relieve repression of immune-modulatory cytokines IL-6 and IL-10. Let-7 has also been implicated in the negative regulation of TLR4, the major immune receptor of microbial lipopolysaccharide and down-regulation of let-7 both upon microbial and protozoan infection might elevate TLR4 signalling and expression.

Let-7 has furthermore been reported to regulate the production of cytokine IL-13 by T lymphocytes during allergic airway inflammation thus linking this miRNA to adaptive immunity as well. Down-modulation of the let-7 negative regulator Lin28b in human T lymphocytes is believed to occur during early neonate development to reprogram the immune system towards defense. Given the prominent phenotype of cell hyperproliferation and undifferentiation by let-7 loss-of-function in nematodes, and the role of its targets on cell destiny determination, let-7 is closely associated with human cancer and acts as a tumor suppressor.

Numerous reports have shown that the expression levels of let-7 are frequently low and the chromosomal clusters of let-7 are often deleted in many cancers. Let-7 is expressed at higher levels in more differentiated tumors, which also have lower levels of activated oncogenes such as RAS and HMGA2. Therefore, expression levels of let-7 could be prognostic markers in several cancers associated with differentiation stages. In lung cancer, for example, reduced expression of let-7 is significantly correlated with reduced postoperative survival.

Let-7 is also a very attractive potential therapeutic that can prevent tumorigenesis and angiogenesis, typically in cancers that underexpress let-7. Lung cancer, for instance, have several key oncogenic mutations including p53, RAS and MYC, part of which may directly correlate with the reduced expression of let-7, and may be repressed by introduction of let-7. Intranasal administration of let-7 has already been found effective in reducing tumor growth in a transgenic mouse model of lung cancer. Similar restoration of let-7 was also shown to inhibit cell proliferation in breast, colon and hepatic cancers, lymphoma, and uterine leiomyoma.

In accordance with the present invention, reduced levels of let-7 indicate polyamine dysregulation, and hence are an indicator that polyamine synthesis inhibition may be effective. Low levels also can indicate that the dosage of the inhibitor is too low for therapeutic effect, whereas an increase in let-7 as compared to a prior measurement indicates that a therapy is effective.

In the Examples below, it was shown that several non-coding RNAs were altered via polyamine depletion. In some embodiments, the let-7 family served as an attractive target to mediate signaling nodes involved in tumorigenesis. In some embodiments, the methods provided herein may be used to treat diseases that exhibit dysregulated let-7, for example, not only colorectal carcinoma, but also neuroblastoma. See Buechner et al., 2011, which is incorporated herein by reference. In some embodiments, the methods provided herein are polyamine inhibitory therapies that may be used to treat neuroblastoma. See Hogarty et al., 2008, which is incorporated herein by reference.

B. LIN28

LIN28 homolog A is a protein that in humans is encoded by the LIN28 gene. LIN28 encodes a miRNA-binding protein that binds to and enhances the translation of the IGF-2 (insulin-like growth factor 2) mRNA. LIN28 has also been shown to bind to the let-7 pre-miRNA and block production of the mature let-7 miRNA in mouse embryonic stem cells.

LIN28 is a marker of undifferentiated human embryonic stem cells and has been used to enhance the efficiency of the formation of induced pluripotent stem (iPS) cells from human fibroblasts. Crystallographic structures of LIN28/ let-7 complexes reveal that two folded domains of LIN28 recognize two distinct regions of the RNA. The domains are sufficient for inhibition of let-7 in vivo.

In accordance with the present invention, increased levels of LIN28 indicate polyamine dysregulation, and hence are an indicator that polyamine synthesis inhibition may be effective. High levels also can indicate that the dosage of the inhibitor is too low for therapeutic effect, whereas a decrease in LIN28 as compared to a prior measurement indicates that a therapy is effective.

C. HMGA2

High-mobility group AT-hook 2, also known as HMGA2, is a protein that, in humans, is encoded by the HMGA2 gene. This gene encodes a protein that belongs to the non-histone chromosomal high-mobility group (HMG) protein family. HMG proteins function as architectural factors and are essential components of the enhancesome. This protein contains structural DNA-binding domains and may act as a transcriptional regulating factor. Identification of the deletion, amplification, and rearrangement of this gene that are associated with lipomas suggests a role in adipogenesis and mesenchymal differentiation. A gene knockout study of the mouse counterpart demonstrated that this gene is involved in diet-induced obesity. Alternate transcriptional splice variants, encoding different isoforms, have been characterized.

The expression of HMGA2 in adult tissues is commonly associated with both malignant and benign tumor formation, as well as certain characteristic cancer-promoting mutations. Homologous proteins with highly conserved sequences are found in other mammalian species, including lab mice (*Mus musculus*).

HMGA2 contains three basic DNA-binding domains (AT-hooks) that cause the protein to bind to adenine-thymine (AT)-rich regions of nuclear DNA. HMGA2 does not directly promote or inhibit the transcription of any genes, but alters the structure of DNA and promotes the assembly of protein complexes that do regulate the transcription of genes. With few exceptions, HMGA2 is expressed in humans only during early development, and is reduced to undetectable or nearly undetectable levels of transcription in adult tissues. The miRNA let-7 is largely responsible for this time-dependent regulation of HMGA2. The apparent function of HMGA2 in proliferation and differentiation of cells during development is supported by the observation that mice with mutant HMGA2 genes are unusually small (pygmy phenotype), and genome-wide association studies link HMGA2-associated SNPs to variation in human height.

Let-7 inhibits production of specific proteins by complementary binding to their mRNA transcripts. The HMGA2 mature mRNA transcript contains seven regions complementary or nearly complementary to let-7 in its 3' UTR. Let-7 expression is very low during early human development, which coincides with the greatest transcription of HMGA2. The time-dependent drop in HMGA2 expression is caused by a rise in let-7 expression.

Heightened expression of HMGA2 is found in a variety of human cancers, but the precise mechanism by which HMGA2 contributes to the formation of cancer is unknown. The same mutations that lead to pituitary adenomas in mice can be found in similar cancers in humans. Its presence is associated with poor prognosis for the patient, but also with sensitization of the cancer cells to certain forms of cancer therapy. Specifically, HMGA2-high cancers display an abnormally strong response to double strand breaks in DNA caused by radiation therapy and some forms of chemotherapy. Artificial addition of HMGA2 to some forms of cancer unresponsive to DNA damage cause them to respond to the treatment instead, although the mechanism by which this phenomenon occurs is also not understood. However, the expression of HMGA2 is also associated with increased rates of metastasis in breast cancer, and both metastasis and recurrence of squamous cell carcinoma. These properties are responsible for patients' poor prognoses. As with HMGA2's effects on the response to radiation and chemotherapy, the mechanism by which HMGA2 exerts these effects is unknown.

A very common finding in HMGA2-high cancers is the under-expression of let-7. This is not unexpected, given let-7's natural role in the regulation of HMGA2. However, many cancers are found with normal levels of let-7 that are also HMGA2-high. Many of these cancers express the normal HMGA2 protein, but the mature mRNA transcript is truncated, missing a portion of the 3' UTR that contains the critical let-7 complementary regions. Without these, let-7 is unable to bind to HMGA2 mRNA, and, thus, is unable to repress it. The truncated mRNAs may arise from a chromosomal translocation that results in loss of a portion of the HMGA2 gene.

HMGA2 has been shown to interact with PIAS3 and NFKB1. The transport of HMGA2 to the nucleus is mediated by an interaction between its second AT-hook and importin-α2.

In accordance with the present invention, increased levels of HMGA2 indicate polyamine dysregulation, and hence an indicator that polyamine synthesis inhibition may be effective. High levels also can indicate that the dosage of the inhibitor is too low for therapeutic effect, whereas a decrease in HMGA2 as compared to a prior measurement indicates that a therapy is effective.

D. Nucleic Acid Detection

Assessing expression of a nucleic acid may involve quantitating RNA. Northern blotting techniques are well known to those of skill in the art. Northern blotting involves the use of RNA as a target. Briefly, a probe is used to target an RNA species that has been immobilized on a suitable matrix (e.g., nitrocellulose). The different species should be spatially separated to facilitate analysis. This often is accomplished by gel electrophoresis of nucleic acid species followed by "blotting" on to the matrix.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished.

Nucleic acids may be quantitated following gel separation and staining with ethidium bromide and visualization under UV light. Alternatively, if the nucleic acid results from a synthesis or amplification using integral radio- or fluorometrically-labeled nucleotides, the products can then be exposed to x-ray film, or visualized under the appropriate stimulating spectra, following separation.

In one embodiment, visualization is achieved indirectly. Following separation of nucleic acids, a labeled nucleic acid is brought into contact with the target sequence. The probe is conjugated to a chromophore or a radiolabel. In another embodiment, the probe is conjugated to a binding partner, such as an antibody or biotin, and the other member of the binding pair carries a detectable moiety.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used. Using the sequences disclosed herein, oligonucleotide primers may be designed to permit the amplification of sequences of interest Reverse transcription (RT) of RNA to cDNA followed by relative quantitative PCR (RT-PCR) can be used to determine the relative concentrations of specific mRNA species isolated from patients. By determining that the concentration of a specific mRNA species varies, it is shown that the gene encoding the specific RNA species is differentially expressed. In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR. amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. β-actin, asparagine synthetase and lipocortin II are examples of mRNAs that can be used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

E. Protein Detection

Antibodies can be used in characterizing protein expression in cells through techniques, such as ELISA and Western blotting. For example, antibodies may be immobilized onto a selected surface, such as a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting the same to a second antibody having specificity for the target that differs from the first antibody. Appropriate conditions include diluting the sample with diluents such as BSA, bovine gamma globulin (BGG) and phosphate buffered saline (PBS)/Tween. These added agents also tend to assist in the reduction of nonspecific background. The layered antisera is then allowed to incubate for about 2-4 h, at temperatures on the order of about 25-27° C. Following incubation, the antisera-contacted surface is washed so as to remove non-immunocomplexed material. A particular washing procedure includes washing with a solution such as PBS/Tween, or borate buffer.

To provide a detecting means, the second antibody may have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions that favor the development of immunocomplex formation (e.g., incubation for 2 h at room temperature in a PBS-containing solution such as PBS/Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will also find use in immunoblot or Western blot analyses. The antibodies may be used as high-affinity primary reagents for the identification of proteins immobilized onto a solid support matrix, such as nitrocellulose, nylon, or combinations thereof. In conjunction with immunoprecipitation, followed by gel electrophoresis, these may be used as a single-step reagent for use in detecting antigens against which secondary reagents used in the detection of the antigen cause an adverse background. Immunologically-based detection methods for use in conjunction with Western blotting include enzymatically-, radiolabel- or fluorescently-tagged secondary antibodies against the toxin moiety are considered to be of particular use in this regard.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; and snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

With regard to immunohistochemical methods, in some embodiments, formalin-fixed paraffin-embedded (FFPE) sections of tissue specimens are placed on positively charged slides (e.g., X-tra Slides, Surgipath Inc. Richmond, Ill.). In some embodiments, the sections may be deparaffinized, for example, with a xylene substitute (e.g., Clear-Rite 3 Cardinal Health, Dublin, Ohio). In some embodiments, the sections are then rehydrated, for example, through decreasing concentrations of 90:5:5 ethyl:methyl:isopropyl alcohol. Antibodies that may be used include: HMGA2 (Cell Signaling, #8179), LIN28 (Abcam, #46020), and eIF5A (Epitomics, #S2096). In some embodiments, immunoperoxidase reactions may be performed using an automated immunostainer (e.g., Ventana BenchMark Ultra, Ventana Medical Systems, Tucson Ariz.). In some embodiments, other reactions may be performed on a Dako® Autostainer Plus or a Ventana® BenchMark. For specimens stained with the Dako® Autostainer, pretreatment is performed using Dako® Target Retrieval Solution, pH 6 (Dako, Inc.) in a pressure cooker for 5 minutes. For specimens stained on the Ventana® BenchMark, automated pretreatment with Cell Conditioning Solution 2, a pH 6 citrate-buffered antigen retrieval buffer, is included among the automated steps. For both, the automated steps may include blockage of endogenous peroxidase, reaction with the primary antibody, reaction with the secondary antibody, and linkage to peroxidase. In some embodiments, the chromogen may be diaminobenzadine. In some embodiments, negative controls may be performed in the same fashion, except that the primary antibody may be substituted with a non-specific (e.g., mouse) immunoglobulin.

F. Predicting Response to Polyamine Inhibition Therapy

Taking into consideration any or all of the markers discussed above, a clinician may predict those subjects that may respond favorably to a therapy based on the inhibition of polyamine synthesis. In this regard, the clinician may choose to compare the marker levels in the subject with one or more different standards—those standards being levels in normal blood or cells (from the patient or a different subject), blood or cancer cells that have been demonstrated to respond or not respond to polyamine synthesis inhibitors, or pre-established levels taking any or all of the foregoing into account.

G. Adjusting Polyamine Inhibition Therapy

Another application of the present invention involves the use of marker levels during the course of a therapy to (a) determine whether a subject is responding to a polyamine inhibitor therapy, or (b) adjust the dosage of a therapy to increase a response. In this regard, the clinician may choose to compare the marker levels in the subject with one or more different standards—those standards being levels in normal blood or cells (from the patient or a different subject), blood or cancer cells from the subject or a patient prior to therapy that have been demonstrated to respond or not respond to polyamine synthesis inhibitors, or pre-established levels taking any or all of the foregoing into account.

X. PHARMACEUTICAL FORMULATIONS AND ROUTES OF ADMINISTRATION

The therapeutic compounds of the present disclosure may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions that may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a symptom associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 h intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

XI. COMBINATION THERAPY

Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as where "A" represents the first agent (e.g., DFMO) and "B" represents a secondary agent (e.g., sulindac), non-limiting examples of which are described below:

| A/B/A   | B/A/B   | B/B/A   | A/A/B   | A/B/B   | B/A/A   |
|---------|---------|---------|---------|---------|---------|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A |         |         |         |         |

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Methods Summary.

HCT116 cells were grown in DMEM media supplemented with 10% fetal bovine serum and cultured at 37° C. For reverse transcription, total RNA was extracted using mirVana RNA isolation kit and reverse transcription performed using Taqman Small RNA Assays with predesigned primer specific to mature let-7 (Applied Biosystems). For microarray, total RNA was extracted from four replicates of DFMO treated and untreated HCT116 cells each after 96 h of incubation and submitted to Asuragen Inc. for processing. Western blots were conducted using anti-HMGA2 (Cell Signaling), LIN28 (abcam), anti-V5 (Invitrogen), eIF5A1 (Epitomics), and Actin (Sigma). Locked Nucleic Acid (LNA) anti-sense oligos were purchased from Exiqon and directed against seed region of let-7 as described previously (Obad et al., 2011). Pre-designed Silencer Select siRNAs (Invitrogen) were obtained to specifically knockdown eIF5A isoforms. All transfections were conducted using Lipofectamine 2000 as described by manufacturer for up to 48 h. All bars show mean±s.d and statistical analysis was performed by using Student's t-test (*$P<0.05$; $P<0.01$, *$P<0.001$).

Tissue Culture and Vectors.

HCT116 cells were maintained in DMEM media supplemented with 5% FBS without antibiotics. Full-length eIF5A2 was cloned into pcDNA6/V5 His vector (Invitrogen). Stably transfected HCT116 cells overexpressing eIF5A2-V5-His were generated and maintained in DMEM containing serum in the presence of blasticidin.

Measurements of Intracellular Polyamine Content.

Cells were homogenized in 0.2 N $HClO_4$. Acid-soluble and acid insoluble fractions were used to determine intracellular polyamines and protein content, respectively. The acid-soluble fraction containing polyamines were separated using reverse-phase ion pair HPLC as described previously (Simoneau et al., 2008).

Cellular Proliferation.

HCT116 cells were seeded in 6-well plates or 100 mm dishes and treated with or without various concentrations of putrescine and DFMO. For data shown, cells were treated with 50 μM putrescine and 5 mM DFMO. At each time point, cells were trypsinized with 500 μL of trypsin and resuspended with 1.5 mL DMEM supplemented with FBS. One milliliter of the resuspension was then loaded and analyzed using a Beckman-Coulter Vi-Cell Counter. Cellular viability was measured through the trypan blue exclusion assay.

RNA Isolation and Real-Time Quantitative RT-PCR.

Total RNA was extracted from cells using the miRVana RNA isolation kit (Ambion) and measured using Thermo Scientific NanoDrop 2000. miRNA levels were measured using an Applied Biosystems 7500 HT PCR instrument with Taqman microRNA assay kits. Controlled reactions were confirmed by excluding reverse transcriptase to confirm amplification from cDNA. Results were analyzed using comparative Ct method between untreated and treated cells. Statistical analysis was performed using two tailed Student's t-tests.

Non-Coding RNA Microarray.

Samples for miRNA profiling studies were processed by Asuragen Services (Austin, Tex.), according to the company's standard operating procedures. Following incoming sample quality control (QC) assessment, the 3' ends of RNA molecules in total RNA samples were labeled with biotin according to the company's standard protocol. Labeled RNA (100 ng total RNA per sample) was purified and hybridized to Affymetrix GeneChip® miRNA Arrays (Affymetrix, Santa Clara, Calif.). Hybridization, washing, staining, imaging, and signal extraction were performed according to Affymetrix-recommended procedures. Arrays were scanned on an Affymetrix GeneChip® Scanner 3000 7G.

Signal Processing.

The signal processing implemented for the Affymetrix miRChip is a multi-step process involving probe specific signal detection calls, background estimate and correction. For each probe, a global robust multichip average (RMA) background correction is performed with Median Polish summarization. Arrays within a specific analysis experiment are normalized together using Quantile normalization. Detection calls are based on a Wilcoxon rank-sum test of the miRNA probe signal compared to the distribution of signals from GC-content matched anti-genomic probes. The raw gene expression data (.cel files) were converted to expression values using the miRNAQCTool, an open-source package available through Affymetrix. This software allows for common options to convert probe level data into expression values, these options include: (1) background correction, (2) normalization (3) probe specific background correction (e.g., subtraction of mismatch probes), and (4) summarization of the probe set values into one measure of expression. RMA selection was used as a normalization method. Permutation P-values were then calculated for the t-test comparison between the DFMO treated and untreated placebo plates. These P-values were then ranked and a candidate gene list was compiled, using false discovery rate (FDR), adjusted P-value cut-offs obtained by the linear step-up method described by Benjamini and Hochberg (1995).

Immunoblot Analysis and Quantification of Western Blot Results.

HCT116 cells were treated with or without DFMO and 50 µM putrescine, harvested by trypsinization, and pelleted at 1000 g for 5 min at 4° C. Cells were then washed twice in cold PBS and then resuspended in RIPA lysis buffer (50 mM Tris, pH 8.0, 150 mM NaCl, 0.1% sodium dodecyl sulphate, 0.5% sodium deoxycholate, 1% TritonX-100 and Complete Mini protease inhibitor tablet and PhosphoSTOP; Roche). Protein concentrations were determined using BCA assay (Pierce). 25-40 µg of whole cell lysate was separated using Any KD or 10% mini-Protean TGX gels and transferred to a PVDF membrane for 1 h at 100 V, and blotted with appropriate antibodies as follows: HMGA2 (Cell Signaling, #8179), LIN28 (Abcam, #46020), Actin (Sigma), V5 (Invitrogen), eIF5A (Epitomics, #S2096). Membranes were washed three times for 10 min and subsequently secondary antibodies were incubated with anti-mouse and anti-rabbit horseradish peroxidase conjugated antibodies (Santa Cruz Biotechnologies). Proteins were visualized by chemoluminescence using Amersham Plus ECL reagent (GE Healthcare). Bands were quantified via Western blot analysis by applying ImageJ software analysis. The amount of specific signal for respective proteins was corrected for sample loading in the displayed diagrams. Briefly, areas under the curves were assessed for each specific band and comparisons were calculated by setting corresponding control values as 100% and each condition corrected by actin.

Oligonucleotides.

The LNA probes were purchased from Exiqon and synthesized using a phosphorothioate backbone. For LNA transfection experiments, HCT116 were pre-treated with DFMO for 48 h and were subsequently transfected using Lipofectamine 2000 (Invitrogen) in 6-well plates with 5 nM, 25 nM, or 50 nM LNA (anti-Let7 LNA: ACTACCTC (SEQ ID NO: 1) or LNA scramble: TCATACTA (SEQ ID NO: 2)). After 48 h whole cell lysate were prepared and analyzed by Western blot.

For eIF5A specific knockdown, Silencer Select siRNAs were purchased from Invitrogen targeting eIF5A1 and eIF5A2. The siRNAs were transfected optimally at 25 nM using Lipofectamine 2000 for 8 h in Opti-MEM. Media was replaced after 8 h of transfection and supplemented with serum containing DMEM. Protein was collected 48 h post-transfection.

Luciferase Reporter Assays.

Hmga2 3' UTR reporter plasmids were obtained from Addgene (Plasmid 14785) and have been characterized in previous studies (Mayr et al., 2007). A mutated Hmga2 reporter plasmid with disrupted let-7 complementary sites was also obtained (Addgene plasmid 14792). HCT116 cells were transfected in 6-well plates with 1.5 µg firefly luciferase and 1.5 µg Hmga2 *Renilla* luciferase reporter plasmids. For functional analysis, 25 nM LNA directed against the let-7 family were transfected with appropriate plasmids. Firefly and *renilla* luciferase were measured 48 h after transfection using a Dual Luciferase Assay (Promega). Results were then normalized to firefly luciferase. Results are mean±SD.

Example 1—Polyamine Depletion Suppresses Growth and Alters Levels of Non-Coding RNAs To address the questions surrounding polyamine's function in cancer, it was reasoned that the polyamines might interact ionically with any number of macromolecules, but could do so strongly with RNA (Watanabe et al., 1991), and covalently with the putative translation factor eIF5A (Saini et al., 2009). It was hypothesized that the polyamines, acting independently or via eIF5A, might affect levels of non-coding RNAs. It was first established that DFMO intervention affected intracellular polyamines resulting in depleted intracellular polyamine pools. DFMO is an irreversible suicide inhibitor of ornithine decarboxylase (ODC) that inhibits carcinogenesis in both mouse models and in humans. Therefore, colon cancer cells were treated with DFMO and the intracellular polyamine pools of cells were measured using high performance liquid chromatography (HPLC). Treatment with DFMO resulted in depletion of putrescine and spermidine in colon cancer cells after 96 h of treatment (FIG. 1A). To address the question of off-targets effects elicited by DFMO treatment, cells were supplemented with the exogenous putrescine, which was shown to restore intracellular polyamine levels, including the hypusine precursor spermidine, in DFMO-treated cells resulting in polyamine levels comparable to vehicle control cells (FIG. 1A).

Figure 1B:
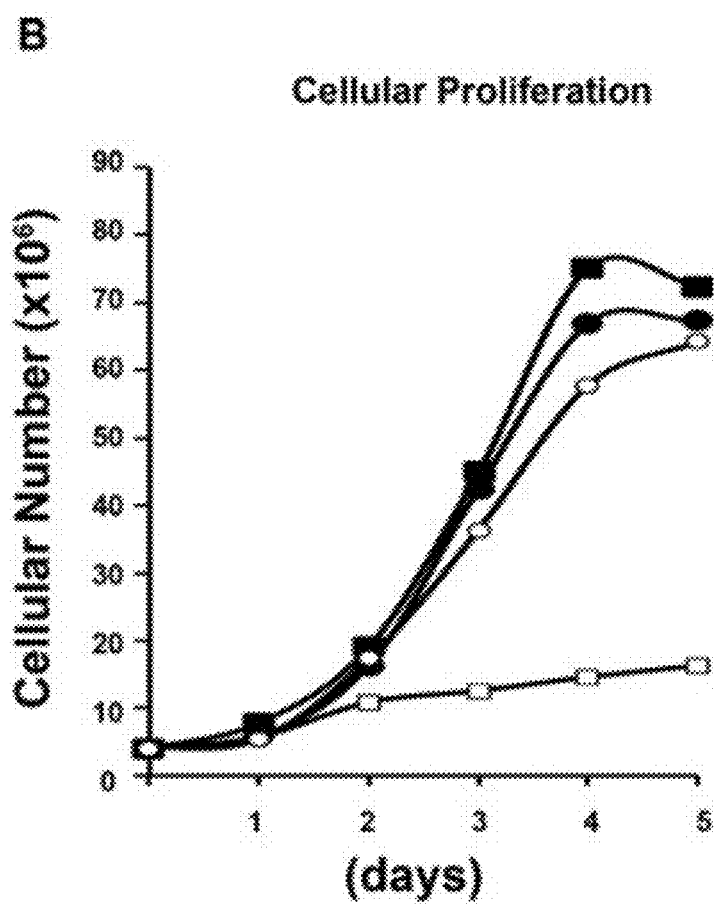

Next, cellular proliferation in HCT116 cells was measured. Depletion of intracellular polyamines was found to reduce cellular proliferation while putrescine supplementation of DFMO-treated HCT116 cells resulted in proliferation rates similar to control levels (FIG. 1B). Proliferation of Caco2 and SW480 colon cancer cells and HeLa cells was also measured. Cellular viability levels were not altered by DFMO treatment. These findings indicated that elevated levels of intracellular polyamine pools are required for proliferation, but that suppression of these levels does not reduce viability of these cells. Furthermore, growth retardation was rescued by exogenous putrescine supplementation of DFMO treated HCT116 cells, indicating that the growth retarding effects of DFMO are due to polyamine depletion and not some unknown off-target drug effect.

Next, the mechanism by which polyamines modulate oncogenesis and the effects of polyamine depletion on non-coding RNA levels was investigated by using a non-coding RNA microarray platform containing 15,644 probes, which included 1105 human mature miRNAs. MicroRNAs (miRNAs) are small endogenous RNA species known to modulate cellular signaling predominantly by binding the 3' untranslated region (UTR) of RNA species. Binding of miRNAs to its cognate target generally results in mRNA destabilization or translational repression (Filipowicz et al., 2008). As a result of the abilities of miRNAs to modulate signaling networks involved in both development and neoplastic diseases, miRNAs serve as attractive targets for disease intervention. Previous reports have demonstrated a role for let-7 in *C. elegans* development (Reinhart et al., 2000), tumorigenesis and cancer development (Kumar et al., 2008; Johnson et al., 2007). Interestingly, polyamines have also been implicated in many fundamental processes affecting normal and neoplastic growth (Gerner and Meyskens, 2004), which have also been shown to be affected by let-7, including its role in regulating cancer associated factors such as HMGA2, KRAS, and MYC (Roush and Slack, 2008).

Multiple non-coding RNAs that are involved in both neoplastic and metabolic diseases as well as in stem cell development were identified as being modulated in a polyamine-dependent manner (Yang et al., 2008). There were 129 probes with permutation P-values <0.05, 65 of those were human miRNA, and there were 14 that remained significant after adjustment for the FDR; seven probes were up-regulated and seven probes were down-regulated (Table 1). Members of the let-7 family, including let-7i, and several other noncoding RNAs were significantly altered by polyamine depletion.

The overlapping pleiotropic effects of polyamines and let-7 strongly suggested that the let-7 family could be part of the mechanism explaining the pharmaceutical action of inhibition of ODC inhibition. Using real-time PCR, the levels of miRNA let-7i were found to be increased after 96 h of ODC inhibition by DFMO treatment in a statistically relevant manner. Thus, the role of polyamines on the let-7 family was elucidated.

TABLE 1

List of non-coding RNAs (ncRNA) affected by polyamine depletion in colorectal cancer cells

| Probe | Mean Expression Level (SD) | | P-value* | Fold Change |
|---|---|---|---|---|
| | Placebo | Treatment | | |
| U50B_x_st | 11.15 (0.05) | 9.86 (0.09) | 0.0276 | −2.44 |
| U50B_st | 11.96 (0.08) | 10.72 (0.18) | 0.0263 | −2.35 |
| U13_st | 11.00 (0.10) | 9.81 (0.26) | 0.0294 | −2.29 |
| U8_st | 10.07 (0.15) | 8.90 (0.23) | 0.0288 | −2.26 |
| U8_x_st | 9.79 (0.17) | 8.86 (0.17) | 0.0267 | −1.90 |
| hsa-miR-193b_st | 9.48 (0.06) | 8.79 (0.15) | 0.0282 | −1.61 |
| hsa-miR-494_st | 13.18 (0.14) | 12.64 (0.05) | 0.0289 | −1.45 |
| hsa-miR-517a_st | 1.00 (0.09) | 1.47 (0.09) | 0.0287 | 1.38 |
| hsa-miR-720_st | 14.00 (0.15) | 14.63 (0.09) | 0.0273 | 1.55 |
| hsa-miR-221_st | 11.68 (0.10) | 12.50 (0.11) | 0.027 | 1.77 |

TABLE 1-continued

List of non-coding RNAs (ncRNA) affected by polyamine depletion in colorectal cancer cells

| Probe | Mean Expression Level (SD) | | P-value* | Fold Change |
|---|---|---|---|---|
| | Placebo | Treatment | | |
| hsa-let-7i_st | 9.68 (0.11) | 10.74 (0.13) | 0.026 | 2.08 |
| hsa-miR-886-3p_st | 10.17 (0.24) | 11.26 (0.15) | 0.0313 | 2.13 |
| hsa-miR-22_st | 8.39 (0.29) | 10.38 (0.09) | 0.0268 | 3.96 |
| hsa-miR-200a-star_st | 2.33 (0.33) | 4.89 (0.59) | 0.029 | 5.88 |

Placebo is the mean expression level for the untreated replicated;
Treatment is the mean expression level for the DFMO treated group;
Fold Change is Treatment versus Placebo;
SD is standard deviation;
*Non-FDR adjusted permutational P-value.

Figure 1C:
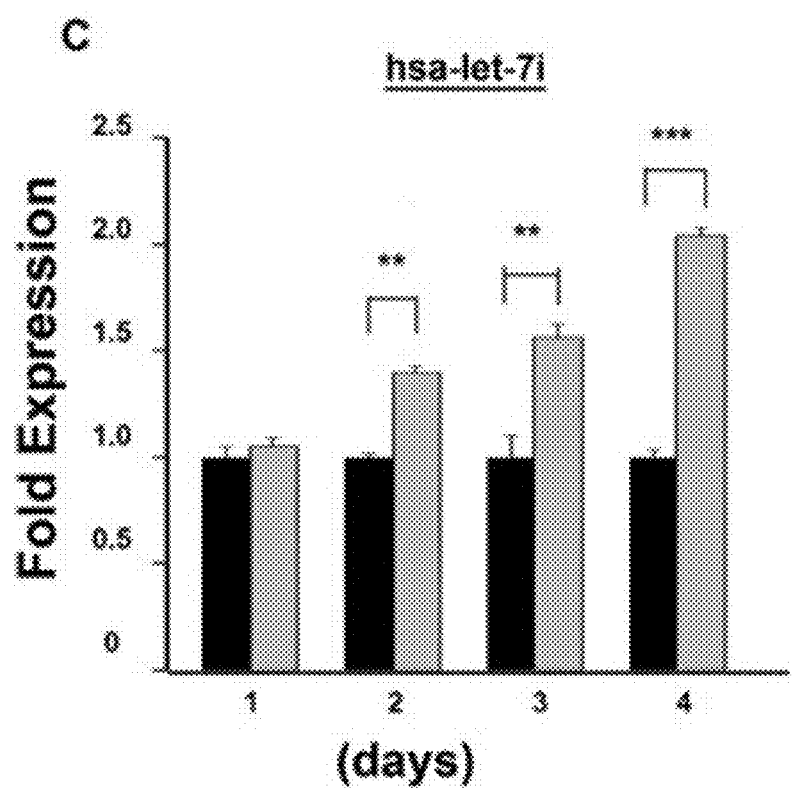
Figure 1D:
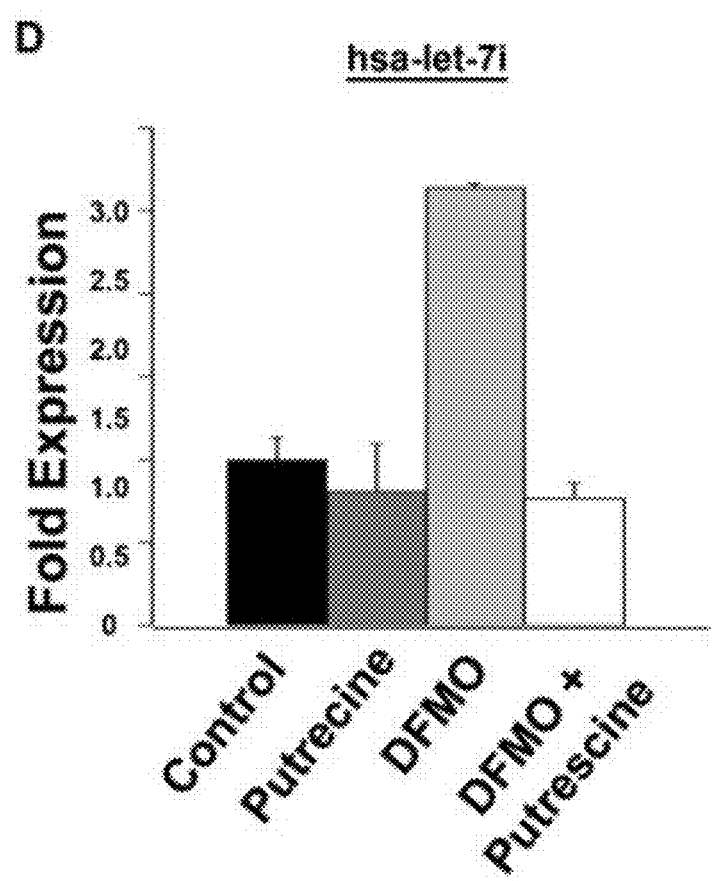

To confirm the microarray results, quantitative PCR analysis was performed in polyamine rich as well as in polyamine-depleted cells. Increased expression of mature let-7i was found in HCT116 cells treated with DFMO in a time-dependent manner with maximal expression occurring at 96 h after initiation of treatment when compared to control (FIG. 1C). The effects of polyamines on another let-7 isoform, let-7a, were measured and similar responses were found, which indicated multiple let-7 family members were in fact regulated by polyamine metabolism. To verify that pharmaceutical intervention was a specific polyamine effect and not due to off target effects, HCT116 cells were treated with putrescine after DFMO administration, isolated total RNA, and measured let-7i expression. Exogenous putrescine rescued the increased levels of let-7i in DFMO treated cells, while having no observable effect in cultures not treated with drug (FIG. 1D). Taken together, these data indicated that members of the let-7 family are modulated by intracellular polyamines and that these amines influence levels of specific microRNAs.

Example 2—Loss of Function of Let-7 Abrogates Polyamine Mediated Effects on HMGA2

Figure 2A:
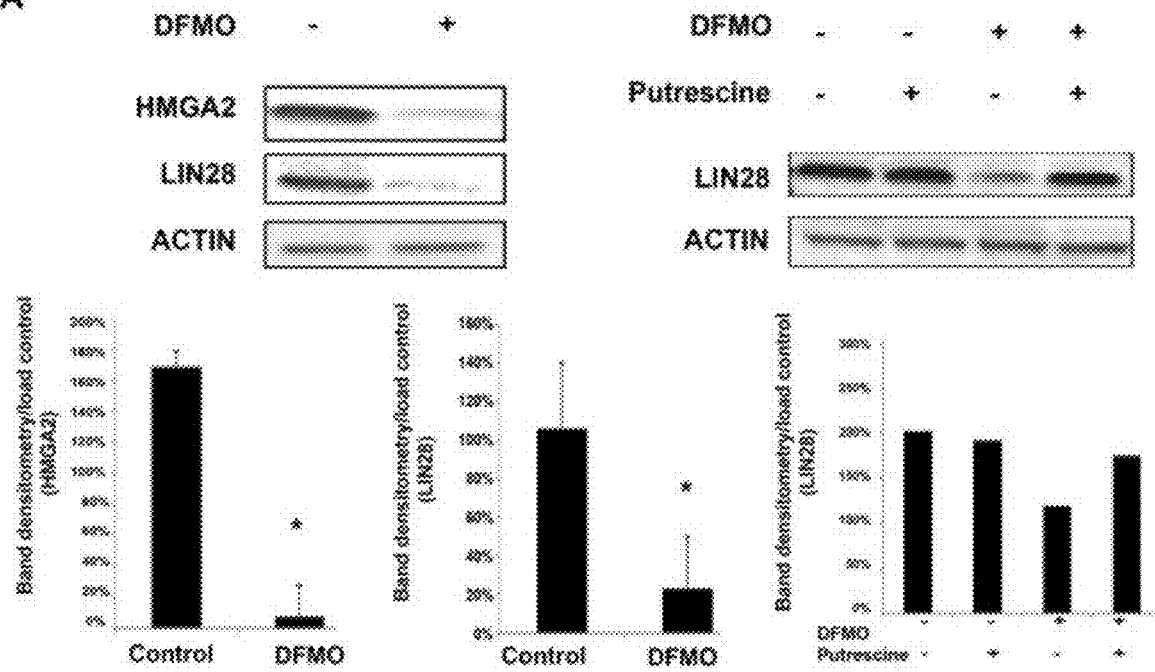
FIGS. 2A-C. Polyamines regulate the let-7 family and alter HMGA2 and LIN28.

To determine if polyamines were influencing specific gene expression via let-7-mediated mechanisms, several putative let-7 target genes were examined. The high mobility group A2 (HMGA2) factor is a previously validated target of let-7 (Mayr et al., 2007; Lee and Dutta, 2007) that is associated with poor survival in colorectal cancer (Wang et al., 2011). Moreover, the HMGA family is widely expressed during embryogenesis and in benign and malignant tumors (Fusco and Fedele, 2007). In order to identify whether polyamines modulated HMGA2 protein levels, cellular polyamines were depleted and Western blots performed, which documented robust HMGA2 depletion by 72 h of DFMO treatment as well as lowered levels of LIN28, the upstream, negative regulator of the let-7 family (FIG. 2A). Next, whether the observed effects were polyamine specific were examined by supplementing the medium of DFMO-treated cells with putrescine. Putrescine supplementation did not alter protein levels of LIN28 in non-drug treated cells. However, putrescine supplementation in DFMO treated cells resulted in LIN28 levels comparable to vehicle control (FIG. 2A), confirming that LIN28 is expressed in a polyamine dependent manner in colon cancer-derived cells.

Figure 2B:
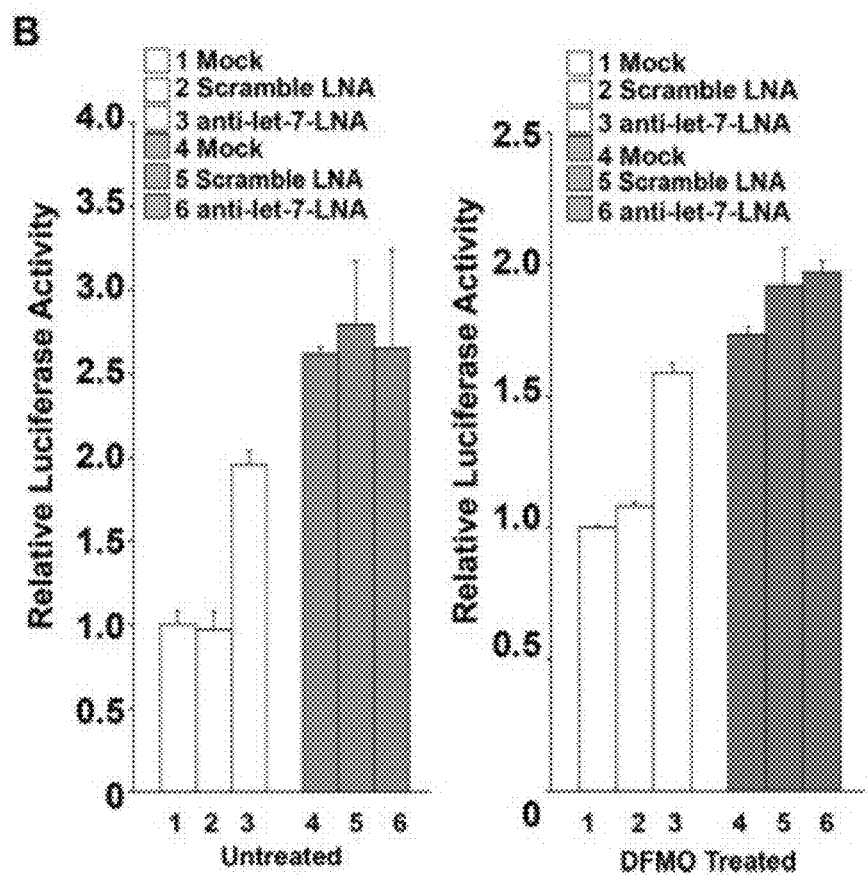

To determine the mechanism of the DFMO-induced reduction of HMGA2, reporter assay was used in which the 3' UTR of Hmga2 was placed downstream of luciferase as reported previously (Mayr et al., 2007). Additionally, a previous report demonstrated the ability to silence miRNA families, such as let-7, with little off target effects by targeting the seed region using locked nucleic acid (LNA) oligonucleotides (Obad et al., 2011). To assess the effects of polyamines on let-7-mediated translational repression of HMGA2, cells were transfected with the Hmga2 3' UTR luciferase reporter containing either intact or mutated let-7 binding sites. Colon cancer cells transfected with a reporter containing intact let-7 binding elements demonstrated diminished reporter activity compared to those cells transfected with reporters containing mutant sequences in the Hmga2 3' UTR. Co-transfection of these plasmids with 25 nM of anti-let-7 LNA, reversed luciferase activities in reporters containing intact let-7 binding elements, but not for reporters containing mutant binding elements (FIG. 2B). Similar results were observed when polyamine pools are depleted by DFMO, indicating that the mechanism of suppression of HMGA2 by let-7 is functional in both polyamine-depleted and polyamine-replete cells. Overall, the Hmga2 3' UTR exhibited enhanced luciferase activity when anti-let-7 LNA oligonucleotides were transfected in both treated and untreated HCT116 cells, but not in control cells transfected with 25 nM scrambled LNAs. A mutant Hmga2 3' UTR luciferase reporter harboring mutagenized putative let-7 target sites was co-transfected and it was observed that mutated Hmga2 3' UTR luciferase activity exhibited higher levels of activity compared to wild-type luciferase reporter. When mock-untreated cells were compared to DFMO-treated mock cells, a reduction in HMGA2 luciferase was observed. Moreover, LNAs directed against let-7 had no observable effect on the mutated 3' UTR Hmga2 vector clearly recapitulating previous reports as well as validating the specificity of the LNA experiments irrespective of polyamine levels (FIG. 2B). Luciferase reporters confirmed that the molecular mechanisms of microRNA mediated translational repression are unaffected in both polyamine rich and polyamine-poor cells suggesting that the increases in let-7 expression due to polyamine depletion result in robust decrease of HMGA2.

Figure 2C:
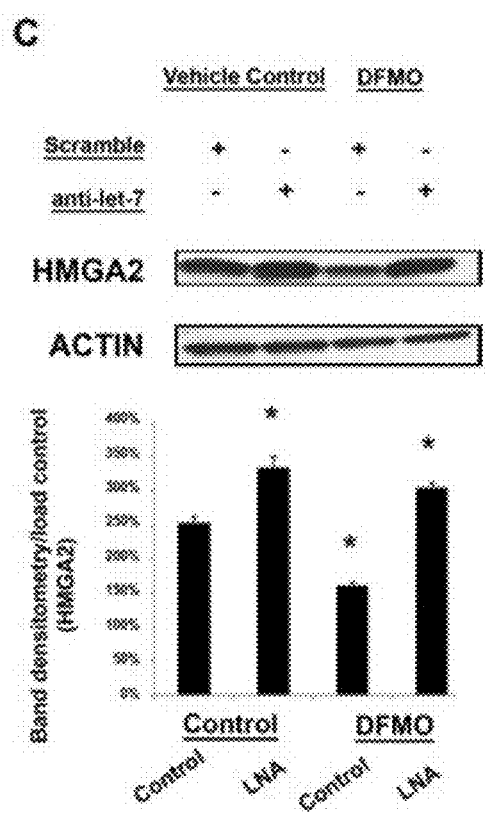

To confirm the HMGA2 reporter data shown in FIG. 2B, mock- and drug-treated cells were transfected with antisense LNA targeting the let-7 family and HMGA2 protein levels were measured (FIG. 2C). Cells treated with DFMO and transfected with scrambled LNA expressed lower HMGA2 levels, compared to untreated cells. LNAs targeting let-7 induced an increase in HMGA2 protein levels in mock-treated cells, while LNAs targeting let-7, but not scrambled LNAs, rescued the DFMO-induced reduction in HMGA2 protein. These results indicated that HMGA2 expression is dependent on polyamines and that the mechanism of polyamine-dependent expression is dependent on let-7 (FIGS. 2A-C). The results in FIGS. 2B-C also highlight the intact function of let-7-mediated translational repression in polyamine depleted cultures.

To gain further insight into the molecular mechanism by which polyamines alter expression of mature levels of let-7i and HMGA2 expression, the effect of polyamine depletion on expression of the let-7 regulator LIN28 was evaluated. LIN28 is a pluripotency factor that binds to precursor let-7 microRNAs and induces uridylation and repression of the let-7 family (Heo et al., 2009). Polyamine depletion resulted in a significant reduction of LIN28 protein after 72 h of drug treatment (FIG. 2A). The DFMO-induced decrease in LIN28 was rescued by exogenous putrescine further indicating the specificity of pharmaceutical intervention (FIG. 2A).

Example 3—eIF5A Regulates HMGA2 and LIN28

Effectors of polyamine metabolism that could account for the widespread changes observed were identified. Polyamines influence protein synthesis, in part, through a novel post-translational modification of eIF5A24. eIF5A is the only protein known to undergo the unique modification called hypusination. Hypusination occurs via a two-step mechanism that includes transfer of a 4-aminobutyl group from the polyamine spermidine to an evolutionarily conserved lysine residue in eIF5A, followed by b-hydroxylation of the deoxyhypusine intermediate. Furthermore, depletion of the hypusine-precursor spermidine by treatment with DFMO causes a corresponding depletion in the hypusinated eIF5A protein (Park et al., 2005). Vertebrates encode two isoforms of eIF5A with differing tissue expression patterns. The eIF5A1 isoform is ubiquitously expressed, but eIF5A2 is found only in specific tissues and some cancers (Caraglia et al., 2011).

Figure 3A:
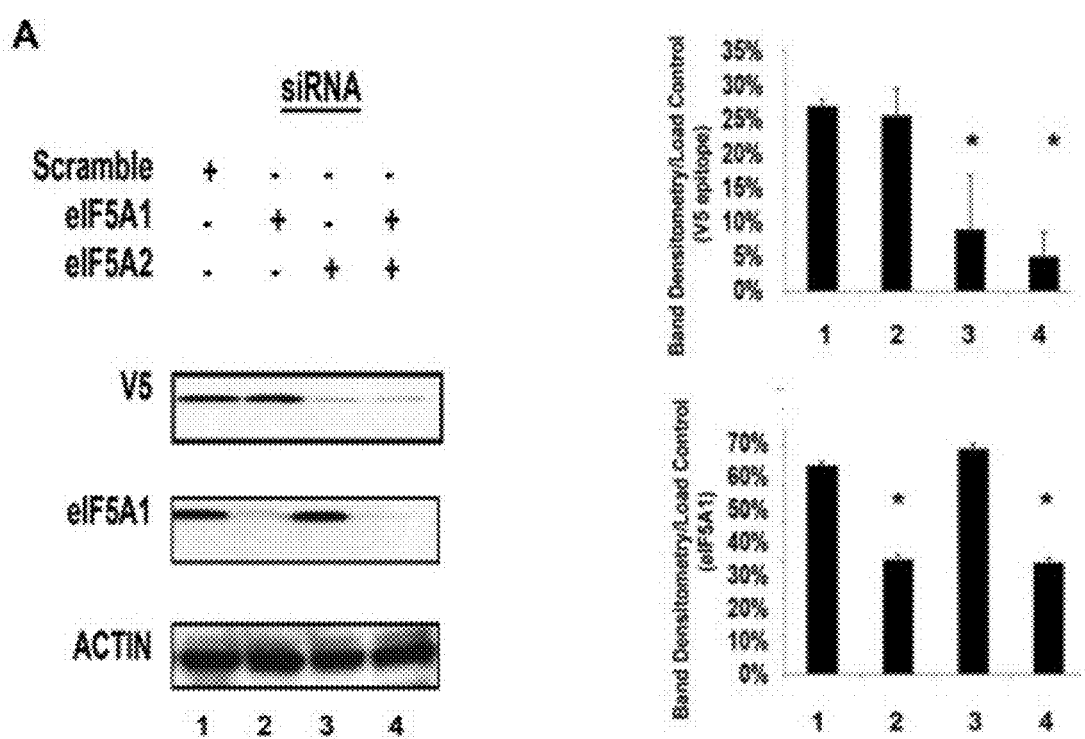
FIGS. 3A-C. eIF5A regulates LIN28 and HMGA2.
Figure 3B:
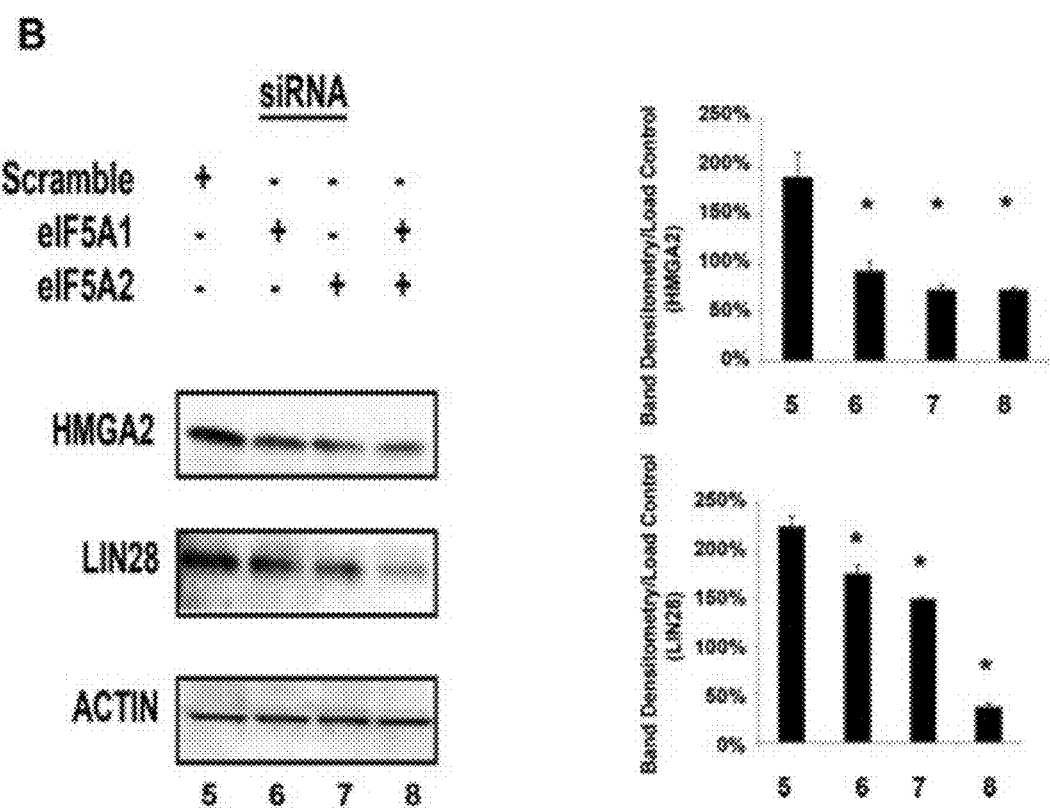
Figure 3C:
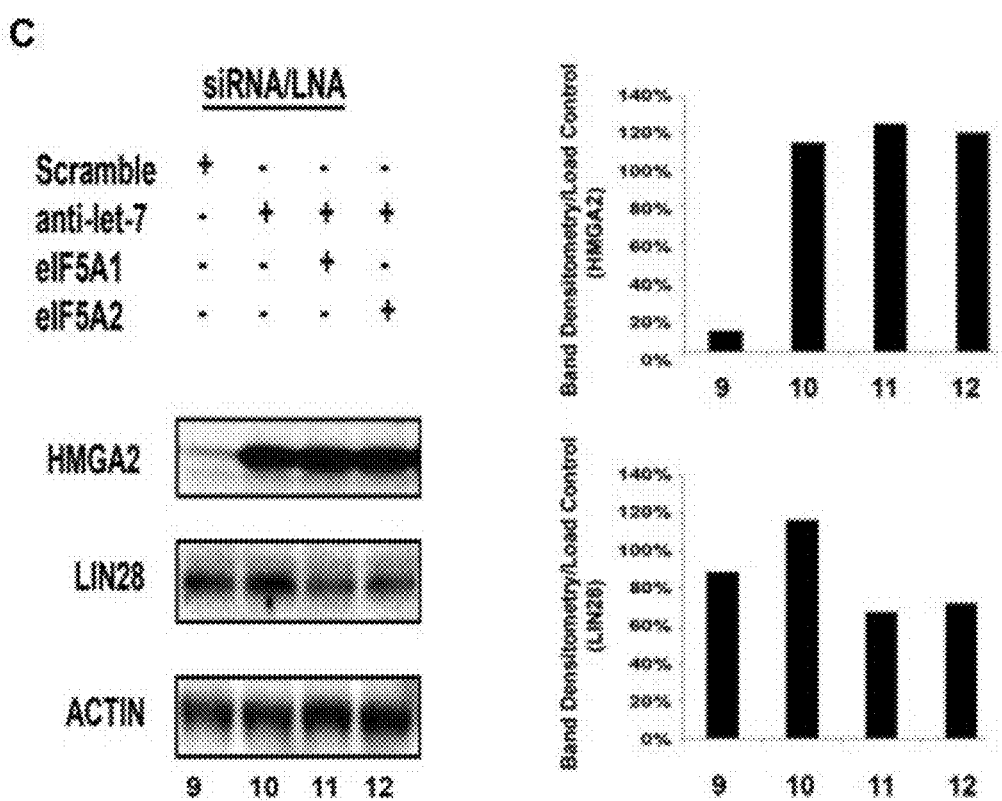
Figure 4:
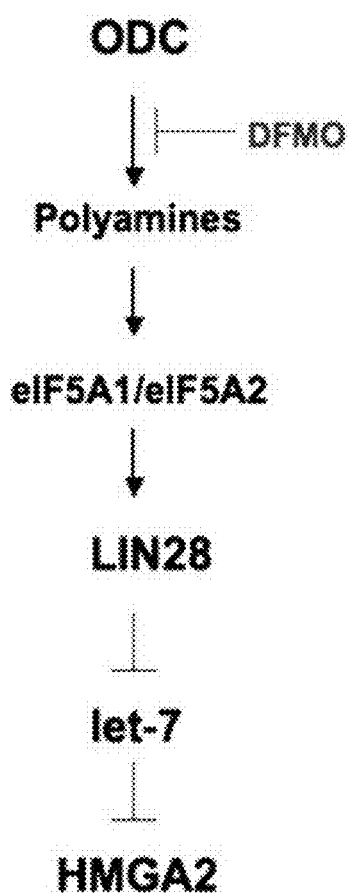
FIG. 4. Model for the effect of polyamine metabolism on the LIN28/let-7 signaling axis and cancer. Tumorigenic cells exhibit deregulated polyamine metabolism through elevated levels of ODC, which is associated with multiple cancers. Elevated levels of polyamines in turn, plays essential roles in cellular processes including maintenance of hypusinated eIF5A for appropriate protein synthesis. eIF5A mediates its effects through microRNA binding proteins, such as LIN28, resulting in negative regulation of let-7, which in turn regulates factors such as HMGA2. When actively dividing cells are depleted of polyamines via agents, such as DFMO, cells are unable to proliferate by maintaining physiological steady-state levels of let-7 and repression of LIN28 and HMGA2. DFMO indicates the pharmaceutical agent used throughout the studies.

Therefore, the possibility that polyamines regulate the LIN28/let-7 pathway through eIF5A was assessed. Given that eIF5A isoforms share considerable amino acid sequence homology and that DFMO targets eIF5A hypusination, an HCT116 stable cell line overexpressing eIF5A2 with a C-terminal V5 epitope was generated to specifically differentiate between both eIF5A isoforms and to further test the potential effects on LIN28/let-7. Seventy-two hours of treatment with 25 nM siRNAs targeting eIF5A1 or eIF5A2 was optimal for specific knockdown of these proteins (FIG. 3A). These conditions were used to determine whether specific knockdown of eIF5A1 or eIF5A2, or both, affected LIN28/let-7 signaling in parental HCT116 cells. The concurrent knockdown of both eIF5A1 and eIF5A2 isoforms consistently resulted in depletion of both HMGA2 and LIN28 (FIG. 3B). Optimal suppression of both of these proteins appeared to be associated with knockdown of both eIF5A1 and eIF5A2 isoforms. LNAs targeting let-7 increased the levels of HMGA2 protein, and this increase was unaffected by knockdown of either eIF5A1 or eIF5A2 (FIG. 3C). In contrast, anti-let-7 LNAs had little effect on LIN28 expression and did not alter the decrease in LIN28 associated with LNAs targeting eIF5A1 or eIF5A2. These data are consistent with the interpretation that polyamines influence expression of specific genes, including HMGA2, by a mechanism involving eIF5A-dependent effects on microRNA-mediated translational repression. These findings suggest a model, depicted in FIG. 4, in which polyamines are oncometabolites that regulate LIN28 expression via eIF5A, and LIN28, in turn, regulates let-7 levels affecting HMGA2 translational repression in HCT116 cells.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 3,647,858
U.S. Pat. No. 3,654,349
U.S. Pat. No. 4,330,559
U.S. Pat. No. 4,413,141
U.S. Pat. No. 5,814,625
U.S. Pat. No. 5,843,929
U.S. Pat. No. 6,258,845
Alberts et al., *J. Cell. Biochem. Supp.*, (22):18-23, 1995.
AMA Drug Evaluations Annual, 1814-1815, 1994.
Babbar et al., *Biochem. J.*, 394:317-24, 2006.
Bailey et al., *Cancer Prev Res (Phila)* 3, 35-47, 2010.
Barry et al., *J. Natl. Cancer Inst.*, 98(20):1494-500, 2006.
Bedi et al., *Cancer Res.*, 55(9):1811-1816, 1995.
Bellofernandez et al., *Proc. Natl. Acad. Sci. USA*, 90:7804-8, 1993.
Buechner et al., *Br J Cancer* 105, 296-303, 2011.
Caraglia et al., *Amino Acids*, epub Dec. 3, 2011.
Childs et al., *Cell. Molec. Life Sci.*, 60:1394-1406, 2003.
Derynck et al., *Nature Genetics*, 29:117-29, 2001.
DuBois et al., *Cancer Res.*, 56:733-737, 1996.
Erdman et al., *Carcinogenesis*, 20:1709-13, 1999.
Filipowicz, et al., *Nat Rev Genet* 9, 102-14, 2008.
Fultz and Gerner, *Mol. Carcinog.*, 34:10-8, 2002.
Fusco, A. & Fedele, M., *Nat Rev Cancer* 7, 899-910, 2007.
Gerner, E. W. & Meyskens, F. L., Jr., *Nat Rev Cancer* 4, 781-92, 2004.
Gerner et al., *Cancer Epidemoil. Biomarkers Prev.*, 3:325-330, 1994.
Giardiello et al., *Cancer Res.*, (57):199-201, 1997.
Guo et al., *Cancer Res.*, 60(22):6314-6317, 2000.
Hanif et al., *Biochemical Pharmacology*, (52):237-245, 1996.
Heo et al., *Cell* 138, 696-708, 2009.
Hogarty et al., *Cancer Res* 68, 9735-45, 2008.
Hubner et al., *Clin. Cancer Res.*, 14(8):2303-9, 2008.
Ignatenko et al., *Cancer Biol. Ther.*, 5(12):1658-64, 2006.
Iwamoto et al., *Carcinogenesis*, 21:1935-40, 2000.
Johnson et al., *Nat. Genet.*, 29(2):233-237, 2001.
Johnson et al., *Cancer Res* 67, 7713-22, 2007.
Kingsnorth et al., *Cancer Res.*, 43(9):4035-8, 1983.
Kumar et al., *Proc Natl Acad Sci USA* 105, 3903-8, 2008.
Ladenheim et al., *Gastroenterology*, 108:1083-1087, 1995.
Landau et al., *J Biol Chem* 285, 12474-81, 2010.
Lanza et al., *Arch. Intern. Med.*, 155:1371-1377, 1995.
Lee, Y. S. & Dutta, A., *Genes Dev* 21, 1025-30, 2007.
Lipkin, *J Cell Biochem. Suppl.*, 28-29:144-7, 1997.
Love et al., *J. Natl. Cancer Inst.*, 85:732-7, 1993.
Luk and Baylin, *N. Engl. J Med.*, 311(2):80-83, 1984.
Lupulescu, *Cancer Detect. Prev.*, 20(6):634-637, 1996.
Martinez et al., *Proc. Natl. Acad. Sci. USA*, 100:7859-64, 2003.
Matsubara et al., *Clinical Cancer Res.*, 1:665-71, 1995.
Mayr et al., *Science* 315, 1576-9, 2007.
McLaren et al., *Cancer Prev. Res.*, 1(7):514-21, 2008.
Meyskens et al., *J. Natl. Cancer Inst.*, 86(15):1122-1130, 1994.
Meyskens et al., *J Natl. Cancer Inst.*, 90(16):1212-8, 1998.
Meyskens et al., Difluoromethylornithine plus sulindac for the prevention of sporadic colorectal adenomas: a randomized placebo-controlled, double-blind trial. *Cancer Prev Res (Phila)* 1, 32-8, 2008.
Muscat et al., *Cancer*, 74:1847-1854, 1994.
Narisawa et al., *Cancer Res.*, 41(5):1954-1957, 1981.
Obad et al., *Nat Genet* 43, 371-8, 2011.
O'Brien et al., *Molec. Carcinog.*, 41(2):120-3, 2004.
Pardali and Moustakas, *Biochimica et Biophysica Acta*, 1775:21-62, 2007.
Park et al., *Amino Acids* 38, 491-500, 2009.
Pegg, *Biochem.*, 234(2):249-262, 1986.
Physician's Desk Reference, Medical Economics Data, Montville, N.J., 1745-1747, 1999
Piazza et al., *Cancer Res.*, (55):311 3116, 1995.
Piazza et al., *Cancer Res.*, (57):2452-2459, 1997a.
Piazza et al., *Cancer Res.*, (57):2909-2915, 1997b.
Pollard and Luckert, *Cancer Res.*, 49:6471-6473, 1989.
Rao et al., *Cancer Res.*, (55):1464-1472, 1995.
Reddy et al., *Cancer Res.*, (50):2562-2568, 1990.
Reddy et al., *Cancer Res.*, 47:5340-5346, 1987.
Reinhart et al., *Nature* 403, 901-6, 2000.
Roberts and Wakefield, *Proc. Natl. Acad. Sci. USA*, 100: 8621-3, 2003.
Roush, S. & Slack, F. J., *Trends Cell Biol* 18, 505-16, 2008.
Saini et al., *Nature* 459, 118-21, 2009.
Samal et al., *Int. J. Cancer*, 133:1323-1334, 2013.
Simoneau et al., *J. Natl. Cancer Inst.*, 93:57-9, 2001.
Simoneau et al., *Cancer Epidemiol Biomarkers Prev* 17, 292-9, 2008.
Singh and Reddy, *Annals. NY Acad. Sci.*, (768):205-209, 1995.
Singh et al., *Carcinogenesis*, (15):1317-1323, 1994.
Sporn, M. B. & Hong, W. K., *Nat Clin Pract Oncol* 5, 628-9, 2008.
Strejan et al., *Cell Immunol.*, 84(1):171-184, 1984.
Su et al., *Science*, (256):668-670, 1992.
Tempero et al., *Cancer Res.*, 49(21):5793-7, 1989.
Thomas and Thomas, *J. Cell Mol. Med.*, 7:113-26, 2003.
Thompson et al., *J. Natl. Cancer Inst.*, (87):125-1260, 1995.
Vander Heiden, M. G. *Nat Rev Drug Discov* 10, 671-84, 2011.
Vane and Botting, *Adv Exp Med Biol.*, 433:131-8, 1997.
Viswanathan et al., *J. Urol.*, 171(2 Pt 1):652-5, 2004.
Viswanathan, S. R. & Daley, G. Q., *Cell* 140, 445-9, 2010.
Viswanathan et al., *Science* 320, 97-100, 2008.
Wallace, *Eur. J Clin. Invest.*, 30:1-3, 2000.
Wang et al., *Clin Cancer Res* 17, 2570-80, 2011.
Watanabe et al., *J Biol Chem* 266, 20803-9, 1991.
Yang et al., *Cancer Res* 68, 10307-14, 2008.
Zhang et al., *Genes Dev* 26, 461-73, 2012.
Zell et al., *Cancer Prev. Res.*, 2(3):209-12, 2009a.
Zell et al., *Clin. Cancer Res.*, 15(19):6208-16, 2009b.
Zender et al., *Cell* 135, 852-64, 2008.
Zhu et al., *Cell* 147, 81-94, 2011.

The invention claimed is:

1. A method for the preventative or curative treatment of cancer in a patient comprising administering to the patient an effective amount of an ornithine decarboxylase (ODC) inhibitor, wherein the patient's cancer has a reduced let-7 non-coding RNA expression level as compared to a reference let-7 non-coding RNA expression level, an elevated HMGA2 protein expression level as compared a reference HMGA2 protein expression level, and/or an elevated LIN28 protein expression level as compared to a reference LIN28 protein expression level.

2. The method of claim 1, wherein the reference level is a level observed in a non-diseased subject or a level observed in a non-cancerous cell from the patient.

3. The method of claim 2, wherein an expression level of a let-7 non-coding RNA, an HMGA2 protein, and/or a LIN28 protein is assessed in a cancer cell from a sample of the cancer obtained from the patient.

4. The method of claim 3, wherein the expression level of a let-7 non-coding RNA is assess using quantitative PCR or Northern blotting.

5. The method of claim 3, wherein the expression level of a HMGA2 protein or LIN28 protein is assessed using immunohistochemistry or ELISA.

6. The method of claim 3, wherein the sample is blood or tissue, such as tumor tissue.

7. The method of claim 3, wherein the patient is a human.

8. The method of claim 3, wherein the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

9. The method of claim 3, wherein the ODC inhibitor is a-difluoromethylornithine (DFMO).

10. The method of claim 3, further comprising administering to the patient a non-steroidal anti-inflammatory drug (NSAID).

11. The method of claim 10, wherein the NSAID is a COX-2 inhibitor.

12. The method of claim 10, wherein the NSAID is sulindac, celecoxib, naproxen, diclofenac, or aspirin.

13. The method of claim 12, wherein the NSAID is sulindac.

14. The method of claim 3, further comprising
obtaining results from a test that determines the expression of a let-7 non-coding RNA in a second cancer cell from said patient at a second time point following the administration of at least one dose of the ODC inhibitor.

15. The method of claim 14, further comprising increasing the amount of the ODC inhibitor administered to the patient if no or a small increase in let-7 non-coding RNA is observed.

16. The method of claim 3, further comprising
obtaining results from a test that determines the expression of a HMGA2 protein and/or a LIN28 protein in a second cancer cell from said patient at a second time point following the administration of at least one dose of the ODC inhibitor.

17. The method of claim 16, further comprising increasing the amount of the ODC inhibitor administered to the patient if no or a small decrease in HMGA2 protein and/or LIN28 protein is observed.

18. The method of claim 10,
wherein the patient's genotype at position +316 of at least one allele of the ODC1 gene promoter is G, wherein the patient is administered combined effective amounts of an ODC inhibitor and an NSAID.

19. The method of claim 3, wherein said cancer is a carcinoma.

20. The method of claim 3, wherein the patient has been diagnosed with familial adenomatous polyposis.

* * * * *